(12) United States Patent
Bleau et al.

(10) Patent No.: US 12,150,884 B2
(45) Date of Patent: Nov. 26, 2024

(54) DYNAMIC ADJUSTABLE SHOULDER ORTHOSIS WITH REHABILITATION BY ADDUCTION

(71) Applicant: 2330-2029 QUÉBEC INC., Montréal (CA)

(72) Inventors: Jacinte Bleau, Boucherville (CA); Mickaël Begon, Montréal (CA); Serge Nobert, Montréal (CA); Marc-andré Dussault, Québec (CA); Raphaël Beaupré-Laflamme, Québec (CA); Jean-christophe Ruel, Québec (CA); Patrice Tétreault, Mont-Royal (CA)

(73) Assignee: 2330-2029 QUÉBEC INC., Montréal (CA)

( * ) Notice: Subject to any disclaimer, the term of this patent is extended or adjusted under 35 U.S.C. 154(b) by 883 days.

(21) Appl. No.: 17/284,622

(22) PCT Filed: Oct. 3, 2019

(86) PCT No.: PCT/CA2019/051420
§ 371 (c)(1),
(2) Date: Apr. 12, 2021

(87) PCT Pub. No.: WO2020/073115
PCT Pub. Date: Apr. 16, 2020

(65) Prior Publication Data
US 2021/0386577 A1 Dec. 16, 2021

(30) Foreign Application Priority Data
Oct. 12, 2018 (CA) .................. CA 3020566

(51) Int. Cl.
*A61F 5/00* (2006.01)
*A61F 5/058* (2006.01)
*A61F 5/37* (2006.01)

(52) U.S. Cl.
CPC ........ *A61F 5/3753* (2013.01); *A61F 5/05858* (2013.01)

(58) Field of Classification Search
None
See application file for complete search history.

(56) References Cited

U.S. PATENT DOCUMENTS 2,661,000 A * 12/1953 Gazeley ................ A61F 5/3753
602/16
5,033,461 A 7/1991 Young et al.
(Continued)

FOREIGN PATENT DOCUMENTS

DE 60209459 T2 8/2006

*Primary Examiner* — Kim M Lewis
(74) *Attorney, Agent, or Firm* — Jacob M. Ward; Ward Law Office LLC

(57) ABSTRACT

A shoulder orthosis is provided for maintenance of a patients arm in a postoperative shoulder immobilization posture in the context of tearing of rotator cuff muscles. The orthosis comprises a belt, an arm splint, and a column member with axial mechanical spring continuously adjustable by a manual adjustment handle and interconnecting the belt to the splint and biasing the splint to an abduction upper limit position. The orthosis provides stable support for the patients forearm around a horizontal plane, while allowing pivoting movement of the patients injured arm about a vertical axis intersecting the patients elbow and approaching the patients torso in a transverse plane. This orthosis also allows a cyclical back and forth movement of the splint, the free downward movement of the patients arm by his healthy muscles, assisted by the adductor muscles against the bias of the adjustable spring without active movement of the rotator cuff. A control handle incrementally locks the spring in a selected retracted position of the axial spring. The axial spring column member remains closely spaced against the (Continued)

patients torso during movements of the splint relative to the patients waist belt.

14 Claims, 34 Drawing Sheets

(56) References Cited

U.S. PATENT DOCUMENTS

| | | | | |
|---|---|---|---|---|
| 5,385,536 | A * | 1/1995 | Burkhead | A61F 5/3753 602/5 |
| 5,487,724 | A | 1/1996 | Schwenn | |
| 9,204,989 | B2 * | 12/2015 | Begon | A61F 5/3753 |
| 9,700,453 | B2 * | 7/2017 | Benenati | A61F 5/3753 |
| 2012/0101419 | A1 | 4/2012 | Bonutti et al. | |

* cited by examiner

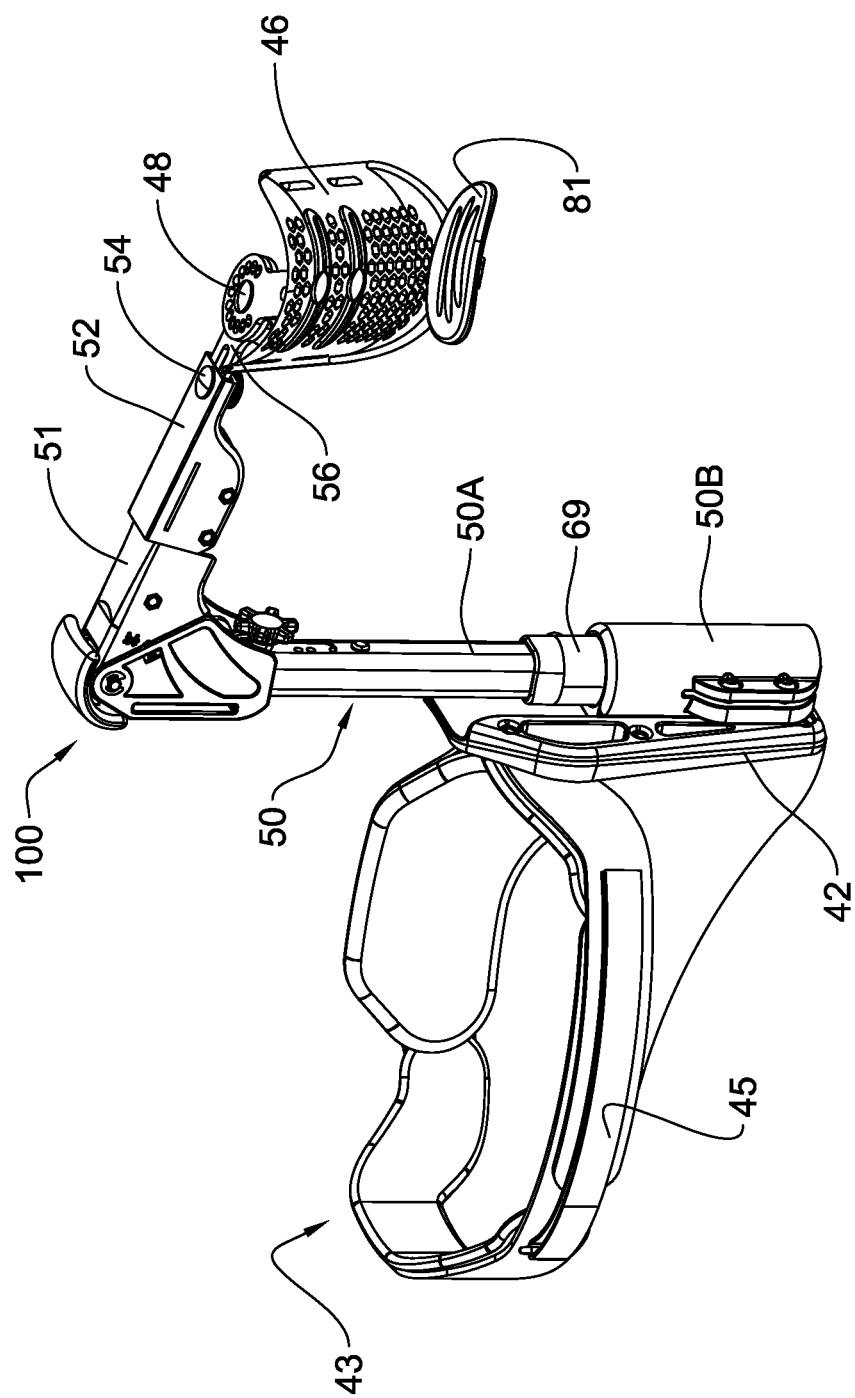

DYNAMIC ADJUSTABLE SHOULDER ORTHOSIS WITH REHABILITATION BY ADDUCTION

CROSS-REFERENCE DATA

This patent application claims convention priority based upon currently co-pending Canadian patent application No 3,020,566 filed 12 Oct. 2018.

FIELD OF THE INVENTION

The present invention relates to a shoulder orthosis for supporting a patient's arm in abduction after post-operative surgical repair of rotator cuff muscle tearing lesions. The shoulder orthosis includes a stabilized height adjustable column member allowing a cyclical exercise of the patient's arm uninjured adductor muscles.

The present invention is therefore a shoulder immobilization orthosis for supporting, in treatment for a shoulder lesion, a patient's injured arm in a prescribed position while the elbow is bent at a right angle in a patient's arm hanging position.

The present invention aims to improve such an orthosis as disclosed in U.S. Pat. No. 9,204,989 issued Dec. 8, 2015 to Université de Montreal jointly with Canadian corporation 2330-2029 Québec inc.

BACKGROUND OF THE INVENTION

Muscular tears are degenerative-type bodily injuries, the occurrence of which increases with age, especially over 50 years old individuals for manual labor or 70 to 80 years old individuals for non-manual labor. Torn shoulder muscle injuries usually occur when a person repeatedly lifts heavy loads over his or her head and appear regularly during sporting activities such as swimming and football matches, professional activities such as window cleaning, and gymnastics and fitness exercises.

An arm splint and sling may be a good initial short-term treatment for any painful shoulder injury. Using a splint helps keep an injured limb from moving. This may temporarily help prevent further injury. Therefore, in a number of cases, a conventional arm sling suffices, provided there is no excessive force on the base of the patient's neck and the sling use is short term. The splint is positioned so the injured limb cannot bend. One should splint from a joint above the injury to a joint below it. To splint an injury, the injured arm is tied to a rigid patient's arm rest. A sling is a bandage used to support and de-weight an injured arm. To apply that sling, the patient's arm needs to be supported above and below the site of the injury, the triangular bandage is placed under the injured arm and over the uninjured shoulder to form a sling, and the bandage opposite ends are tied around the back of the neck.

However, for more than three weeks duration of treatment of shoulder lesions, shoulder orthosis will usually be required, especially after post-operative surgical repair of rotator cuff. A significant portion of the medical treatment of a repaired shoulder muscle may require stabilization and patient's injured arm support in abduction (i.e. away from the patient's sagittal plane) during the healing period associated with the rehabilitation, which usually lasts from four to twelve weeks. Muscle injuries to the shoulder can be of different types and involve different sets of muscles. Different medical treatments involving surgery may be required depending on the type and severity of the injury. In each case, proper healing requires that the patient's arm be stabilized at a specific angle to the body to maintain the shoulder in the optimal position for rehabilitating the injured muscle. As healing progresses, the angle of stabilization of the patient's injured arm is often reduced, bringing the injured arm into adduction (closer to the patient's sagittal plane), that is, progressively closer to its natural position along the body. In addition, these lesions generally affect only a portion of the shoulder muscles, often the supra-spinatus muscle (and possibly also with the infra-spinatus), the length of the tear generally varying between 1 and 20 mm; the other muscles of the shoulder remaining healthy and without lesions. All the abduction brace do immobilize all of the patient's injured arm shoulder, elbow and wrist.

After an initial healing period, it is recommended to progressively start loading once again the muscle of the remaining healthy (i.e. uninjured) shoulder muscles, including the pectoralis major muscle and possibly the latissimus muscle—to maintain the tone of these healthy muscles. This exercise is limited to a certain set of movements that minimize the use of injured or repaired muscles. For example, in many types of rotator cuff injuries, after a certain period of healing, the patient is advised to repeatedly exercise his adduction muscles. When the patient's injured arm immobilization lasts more than about three weeks, ankyloses and atrophy will occur in the upper limbs.

Numerous patient's shoulder orthoses and arm stabilization devices known in the state of the art may be used to stabilize the arm in a single given static position. Other prior art devices provide adjustment mechanisms to change the height at which the patient's arm is stabilized. But these known mechanisms of patient's arm height adjustment often require external intervention and cannot be used without external help. Some also require complex or lengthy procedures, requiring first removal of the orthosis, or involving spare parts, or even special tools. Some also have unstable harnesses and splints relative to the patient's body, or they have several support structures that are often cumbersome and uncomfortable.

In addition, most of these orthoses allow no movement of the free uninjured patient's arm, which is a major disadvantage when several weeks of rehabilitation are needed. In addition, orthotics known in the art do not allow the forearm flexion/extension of the forearm around the elbow of the patient's injured arm.

The aforementioned U.S. Pat. No. 9,204,989 discloses a shoulder orthosis for surgically repaired rotator cuffs, and more specifically for surgically repaired rotator cuff muscles after tearing of the supra-spinatus muscle group only or for the combination of the supra-spinatus and infra-spinatus muscles. This shoulder brace allows for muscle conditioning exercises of the other healthy muscles of the patient's arm while minimizing muscle contraction and stress with rotator cuff injury. This shoulder brace also allows the flexion/extension of the patient's forearm around the elbow while keeping the patient's arm generally horizontal at a constant height. This shoulder brace also stabilizes the arm at different angles relative to the nature of the body, the severity and the healing level of the wound. Flexion/extension of the patient's elbow without arm movement allows activation of the elbow flexors/extensors (biceps and triceps), as well as being more functional and allowing the patient's forearm to be brought closer to the patient's torso. This facilitates daily activities, such as engaging a narrow door frame, donning and wearing a coat and drawing sheets towards the patient's torso while in bed. The orthosis allows the movement of the shoulder and elbow, to prevent the syndrome of "frozen shoulder" and stiffness of the joints.

In general, the invention disclosed in U.S. Pat. No. 9,204,989 relates to a shoulder orthosis intended to withstand in the long term (several weeks) the arm of a patient in a postoperative shoulder immobilization posture with a torn rotator cuff including a waist belt, an arched forearm support, and a piston and cylinder assembly connecting the belt to the forearm support and forcing the forearm support to an upper limit position. This orthosis thus provides some forearm support around a horizontal plane, while allowing pivoting movement of the patient's arm about a vertical axis intersecting the patient's elbow and approaching the patient's torso in that area.

This orthosis also allows a cyclical movement up and down the forearm support, the downward movement being well assisted by an adductor against the bias of the piston/cylinder assembly. A locking system releasably locks the piston and the cylinder in a selected retracted position of the piston rod.

A feature of the orthosis disclosed in prior U.S. Pat. No. 9,204,989 is that the piston and cylinder assembly interconnecting the waist belt to the patient's injured arm supporting splint diverges upwardly outwardly from the waist belt progressively away from the patient's torso to reach the injured arm elbow far away from the injured arm shoulder. Therefore, a sector-shape gap is formed between the piston and cylinder assembly and the patient's torso. Accordingly, donning a shirt or coat can become a challenge because the shirt/coat sleeve will extend over only outer forearm part of the injured arm but will not extend beyond the elbow. An awkward shirt/coat engagement may thus result.

U.S. Pat. No. 9,204,989 also relates to a method of using a shoulder orthosis, said method comprising the steps of: attaching said belt to the size of the patient; attaching the patient's arm to said arm splint; deactivating said locking means; and engaging the adductor muscles of the patient to at least partially retract said connector member from said first fully extended boundary condition to said second boundary condition thereof; wherein the axial spring arm remains directly applied to the patient's torso during movements of the splint relative to the patient's support belt.

OBJECTS OF THE INVENTION

An object of the present invention is therefore to increase a shoulder orthosis intrinsic stability in translation of the patient's injured arm as supported by the orthosis splint arm supporting cradle.

Another object of the invention is to provide a better adjustment of the rehabilitation mechanism.

Another object of the invention is to orient the column member axial spring member so that it generally rests against the torso of the patient (instead of diverging obliquely as with the aforementioned U.S. Pat. No. 9,204, 989) so it makes it easier for the patient to put on or take off a coat without removing the orthosis each time

SUMMARY OF THE INVENTION

Generally speaking, the invention relates to a shoulder orthosis for maintenance of a patient's arm in a postoperative shoulder immobilization posture in the context of tearing of rotator cuff muscles. The orthosis comprises a belt, an arm splint, and a column member with axial mechanical spring continuously adjustable by a manual adjustment handle and interconnecting the belt to the splint and biasing the splint to an abduction upper limit position. The orthosis provides stable support for the patient's forearm around a horizontal plane, while allowing pivoting movement of the patient's injured arm about a vertical axis intersecting the patient's elbow and approaching the patient's torso in a transverse plane. This orthosis also allows a cyclical back and forth movement of the splint, the free downward movement of the patient's arm by his healthy muscles, assisted by the adductor muscles against the bias of the adjustable spring without active movement of rotator cuff. A control handle incrementally locks the spring in a selected retracted position of the axial spring. The axial spring column member remains closely spaced against the patient's torso during movements of the splint relative to the patient's waist belt.

Accordingly, the present invention more specifically relates to a shoulder orthosis for support of a patient's arm in a postoperative angularly adjustable shoulder immobilization abduction posture in a context of injured rotator cuff muscle tear, said orthosis comprising: a) a waistband belt member, for adjustably fitting around the patient's waist, and defining a belt support section; b) a splint, defining a rigid main body having opposite outer and inner end portions, for removably supporting a patient's injured arm; c) an elongated column member, defining top and bottom end portions, said bottom end portion thereof anchored to said belt support section and said top end portion thereof anchored to said inner end portion of the splint; d) joint means interconnecting said splint inner end portion to said column member top end portion for relative movement of said splint thereabout; e) biasing means, cooperating with said column member in providing resistance to patient's injured arm adduction at said splint; f) locking means, applying tension on said biasing means in a conditioning exercise mode of said orthosis, and releasably locking said extensible connector column member in a selected angular orientation relative to said splint, whereby said splint forms a cantilever with said column member; and g) chord adjustment tensioning means, cooperating with said biasing means in enabling transmission of patient's injured arm adduction movement at said splint;

wherein said orthosis allows the cyclical exercise of the healthy adductor muscles of the patient's injured arm while minimizing the contraction of the injured arm rotator cuff muscles.

In one embodiment, there is further included telescopic extension means providing adjustable extension of the length of said elongated column member.

In one embodiment, an axial spring means cooperates with said column member and biases said splint away from said waistband belt member, wherein said spring means allows cyclical extension/retraction of said adjustable length column member between opposite first and second limit conditions thereof; characterized in that said column member remains closely spacedly applied against the patient's torso during movements of the splint relative to the patient's waistband belt.

In one embodiment, said locking means consists of a spring-loaded twist activated plunger, anchoring said axial coil spring means in an operative condition whereby tension is applied onto said coil spring means in the conditioning exercise mode of said orthosis, and releasing said axial coil spring means in an inoperative condition thereof, and pin means cooperating with said column member in setting a lower threshold limit stop for minimal angular inclination between said splint relative to said column member.

In one embodiment, said axial spring means would consists of an elongated compression coil spring member coaxially mounted lengthwisely inside said column member within a telescopic female tubular member therein, and engaging at its top end a male tubular member within said female tubular member and said chord adjustment tensioning means being an internal chord at a bottom end thereof, carried by a seat transversely mounted integral to said column member bottom end portion, characterized in that said internal chord provides transmission of the adduction movement, while coil spring member inside column member provides resistance to adduction of the patient's injured arm.

In one embodiment, said joint means provides internal/external rotation capability of the splint main body relative to said column member. Said joint means could then further provide angular tilt capability of the splint main body relative to said column member, whereby said splint main body would be movable in translation between a first fully extended abduction limit condition and a second retracted adduction limit condition, angularly with respect to the patient's torso.

There could be provided a flexible elongated sling band anchored at one end to a section of said waistband belt and forming a loop around the patient's uninjured shoulder at another end thereof opposite said one end thereof.

In one embodiment, there is provided an elongated forearm support cradle, integrally carried at said outer end portion of the splint main body and defining a free end portion opposite said splint main body. A hand-rest member could then be added, carried by said cradle at said free end portion thereof. Multiple moisture ventilation perforations could also be made in said cradle.

In one embodiment, said joint means provides angular tilt capability of the splint main body relative to said column member, for example with an angular tilt capability selected from the following discrete values: 30°, 45°, 60° and 75°.

In one embodiment, said belt member includes a hook and loop fastener means enabling width adjustment of said waistband belt, the latter being also padded for added patient's comfort and adapted for right or left shoulder injuries.

In one embodiment, there is provided a cradle telescoping means providing adjustable coaxial displacement of said cradle relative to said splint main body, and/or lengthwise cradle telescopic adjustment means for lengthwise cradle extension/retraction; and/or cradle roll adjustment means cooperating with said cradle telescopic adjustment means for rolling motion of said cradle.

The present invention also relates to a method of using such a shoulder orthosis, wherein said method comprises the following steps:—attaching said waistband belt to the patient's waist; —attaching the patient's arm to said splint; —deactivating said locking means; and—engaging the patient's adductor muscles to at least partially retract said connector column member from said first fully extended limit condition to said second limit condition thereof; characterized in that said column member remains closely spacedly applied against the patient's torso during movements of the splint relative to the patient's waistband belt.

The shoulder orthosis according to the present invention enables adjustment of internal and external rotation for different patients, to control shoulder abduction, which was not possible with prior art shoulder orthosis.

BRIEF DESCRIPTION OF THE FIGURES OF DRAWINGS

FIGS. 5, 6, 7 and 8 are views similar to FIGS. 1-4 respectively but with the patient's transverse injured arm support splint and splint cradle tilted upwardly;

FIG. 11B is an enlarged sectional view of the intermediate arm joint of FIG. 11A;

Figure 11:
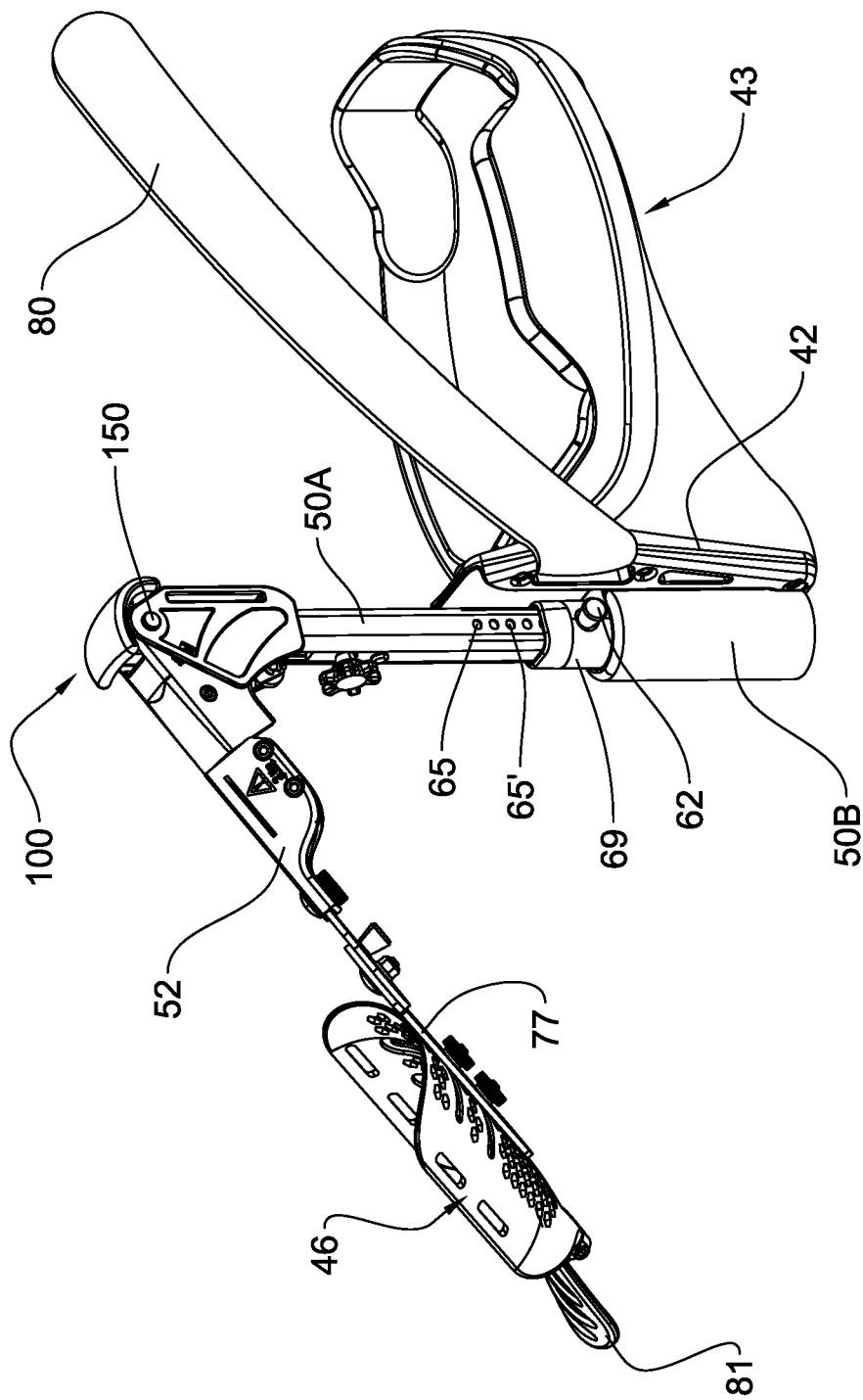
FIG. 11 is a view similar to FIG. 3 but showing an alternate embodiment of the invention where a shoulder strap for engagement with the other uninjured patient's arm could be added to the waist belt and with the splint cradle rotated.
Figure 14:
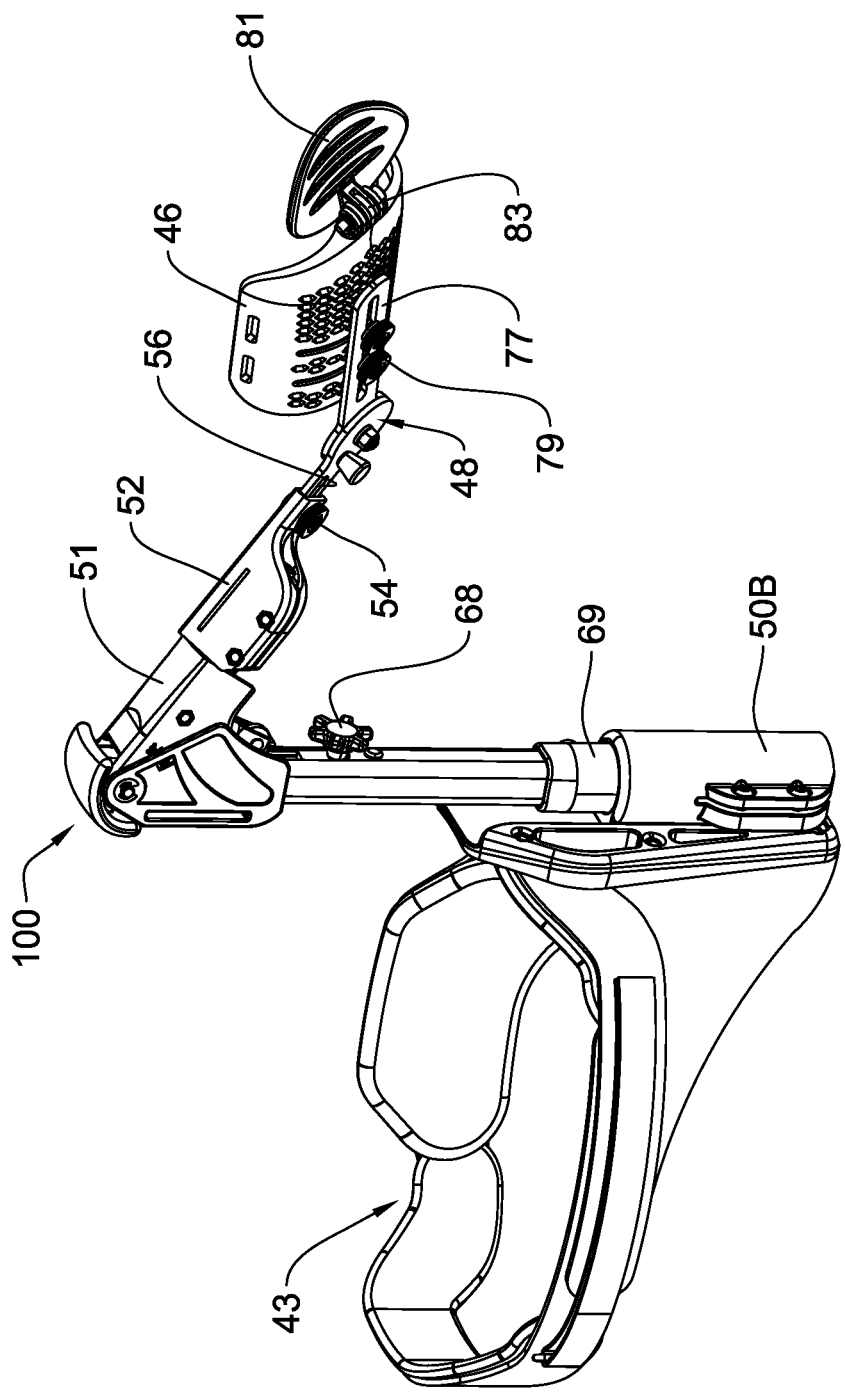
FIG. 14 is a view similar to FIG. 2 but suggesting tilting and rotation motion of the injured arm splint tilted and rotated relative to their position in FIG. 2.
Figure 15:
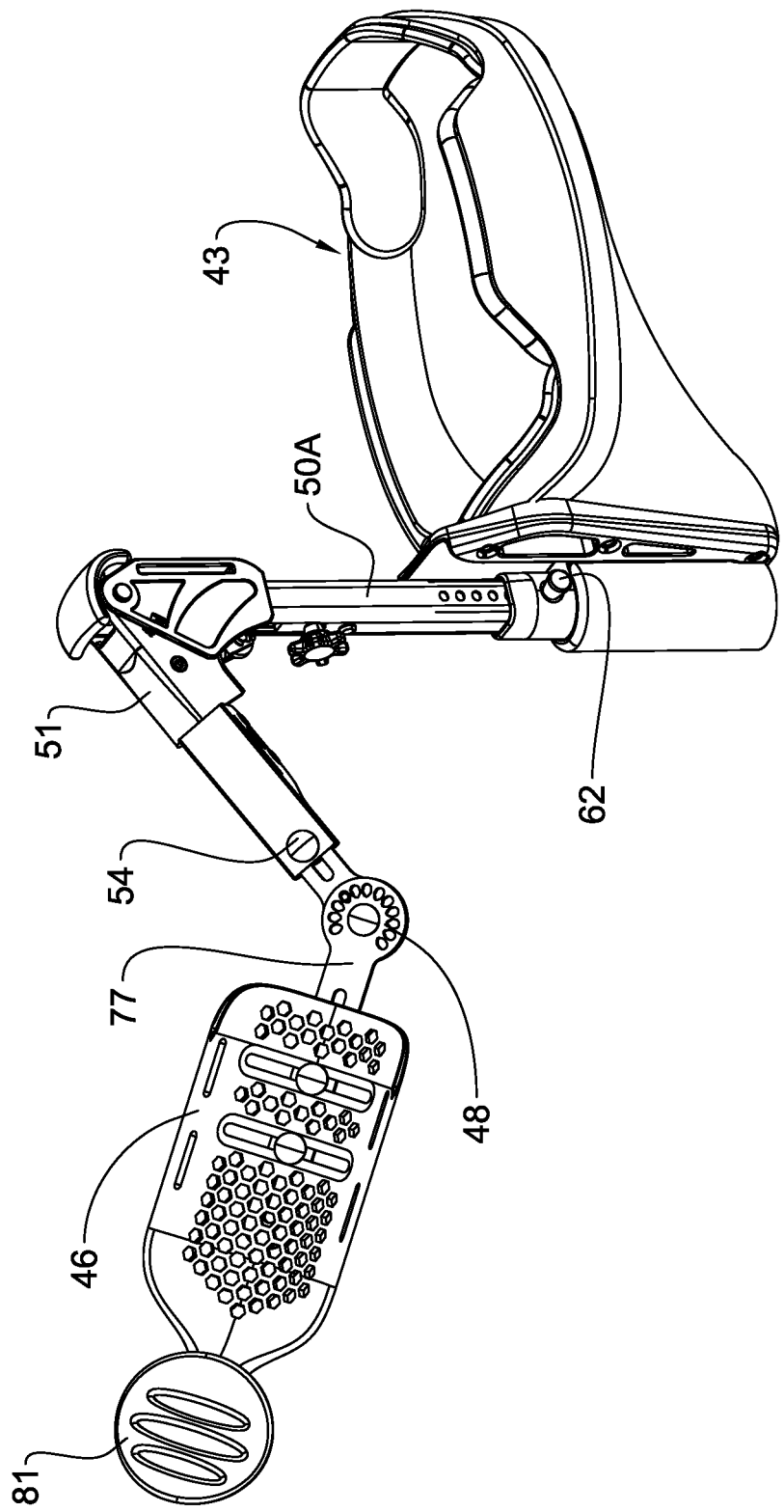
FIG. 15 is a view similar to FIG. 3 but with the relative splint positioning of FIG. 14.
Figure 16:
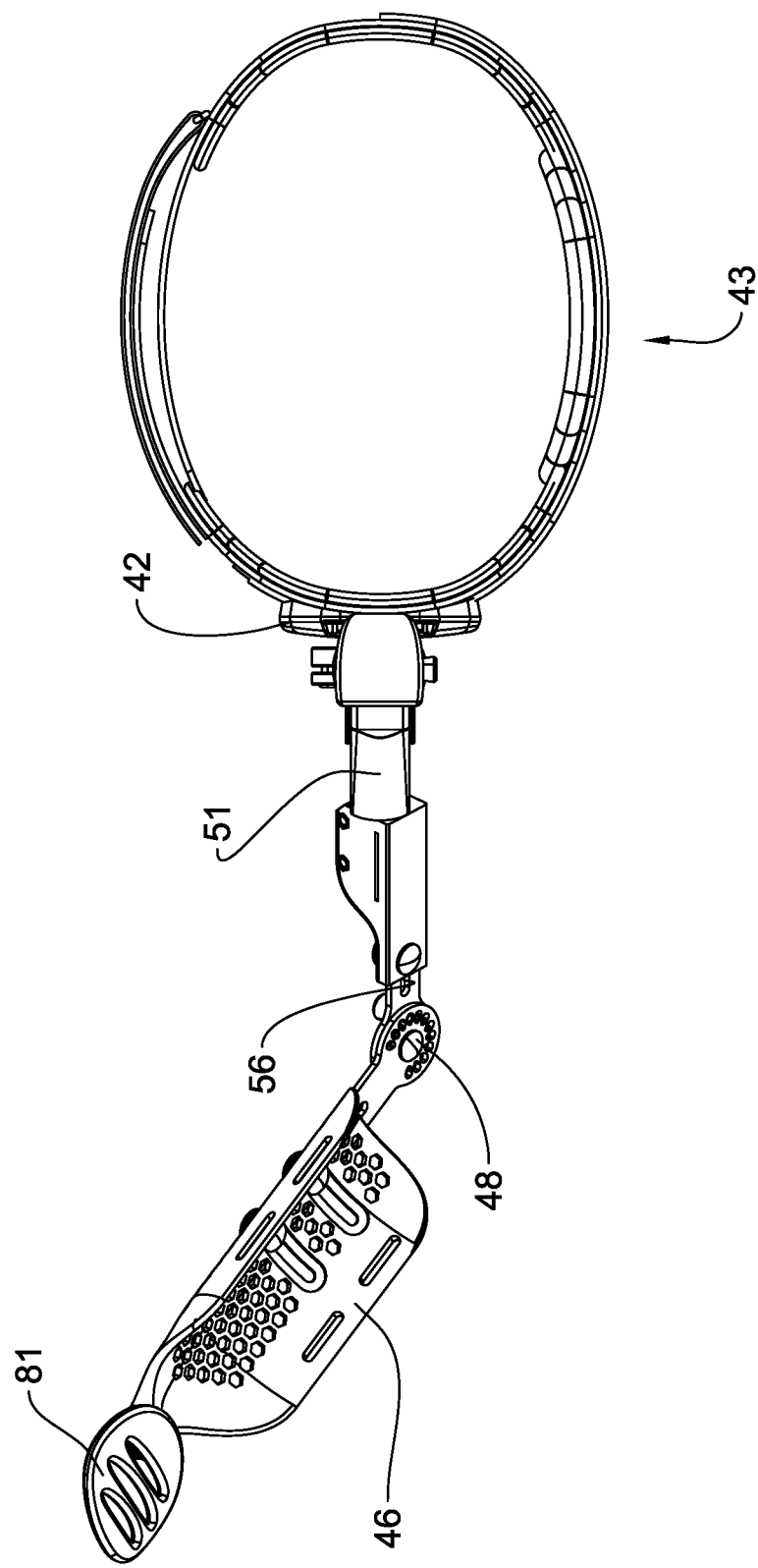
FIG. 16 is a view similar to FIG. 12 but with the relative splint positioning of FIG. 14.
Figure 18:
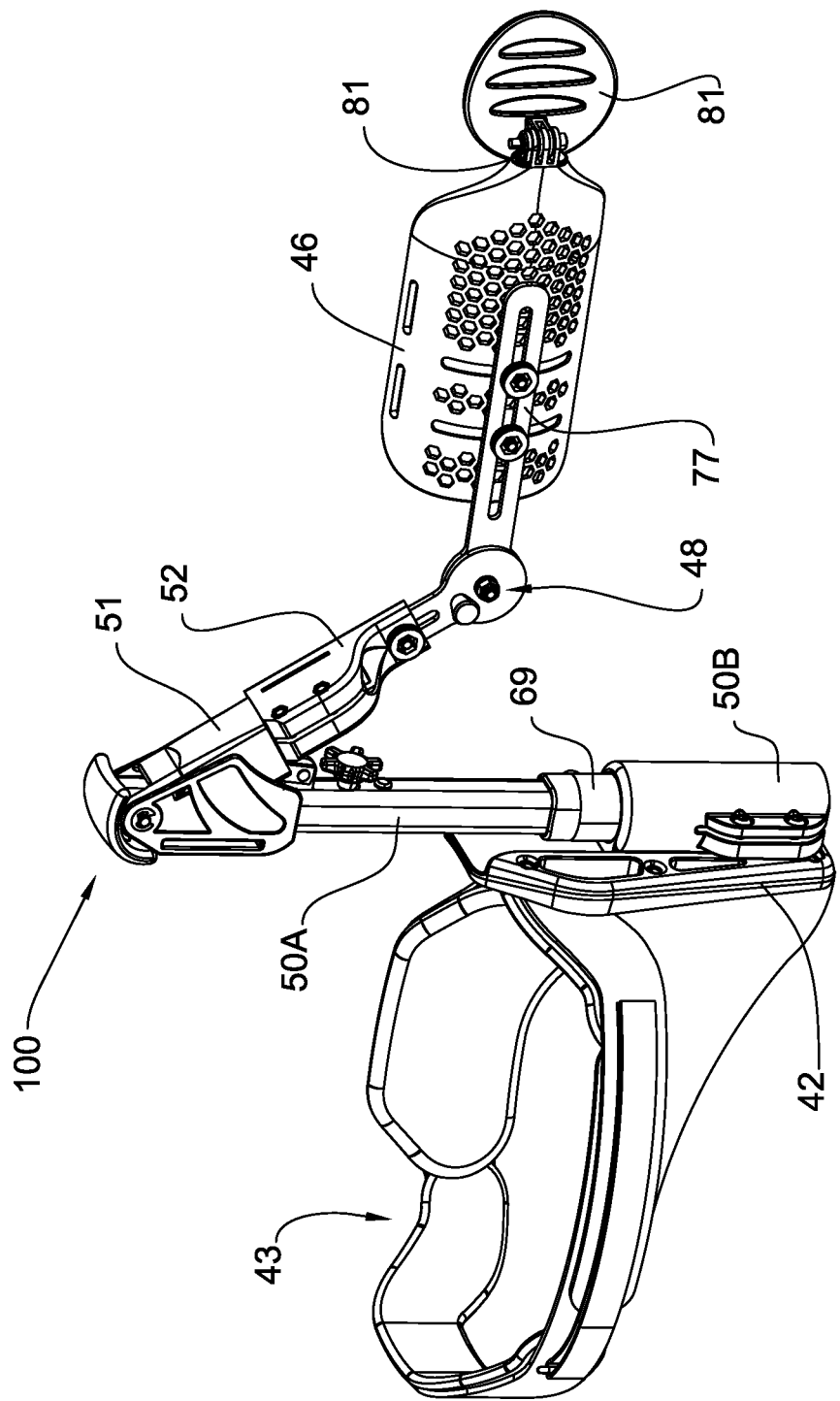
Figure 19:
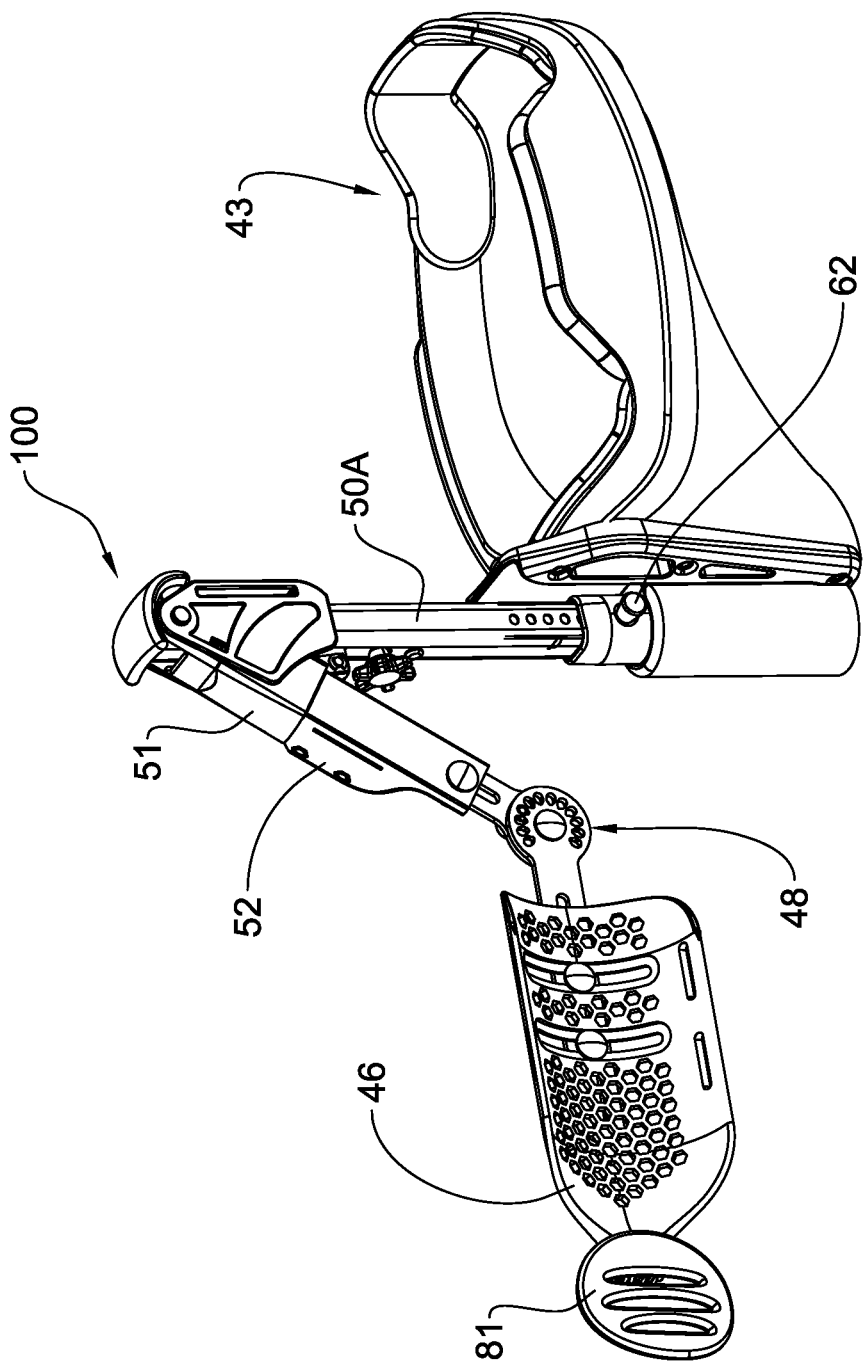
Figure 20:
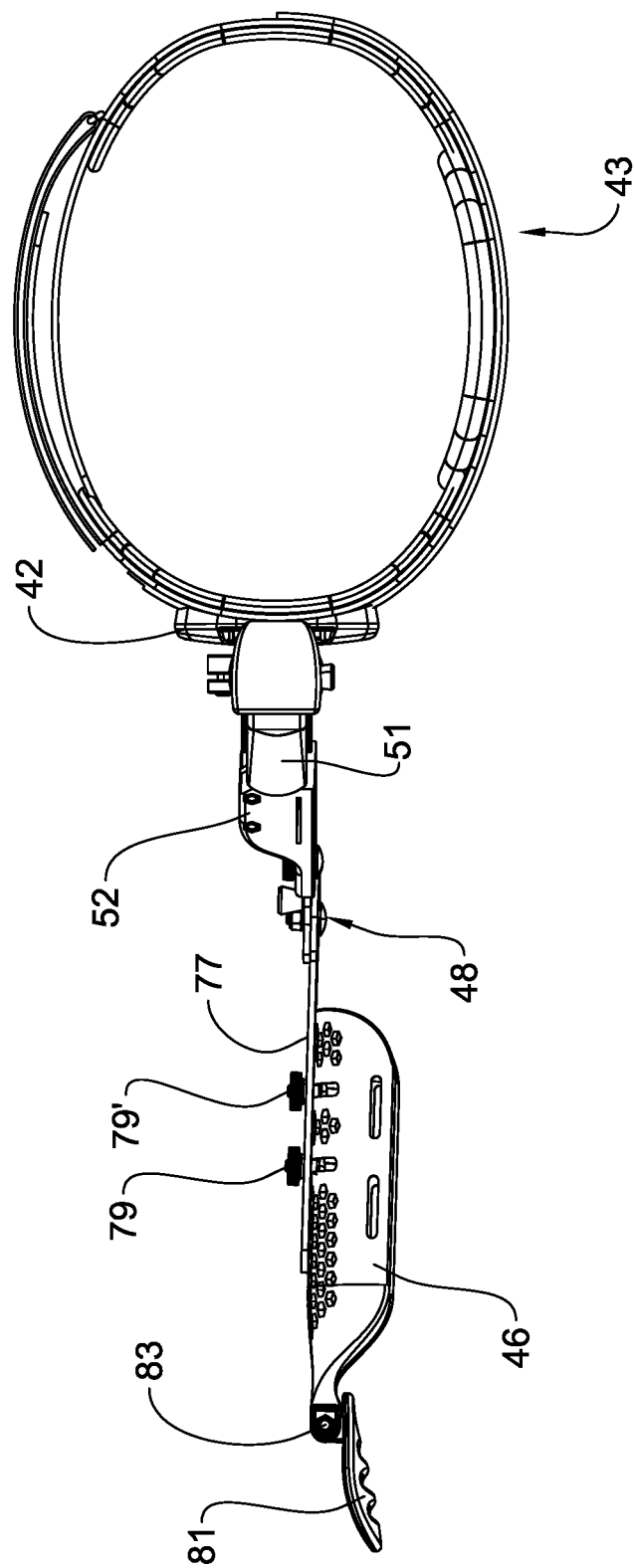
Figure 21:
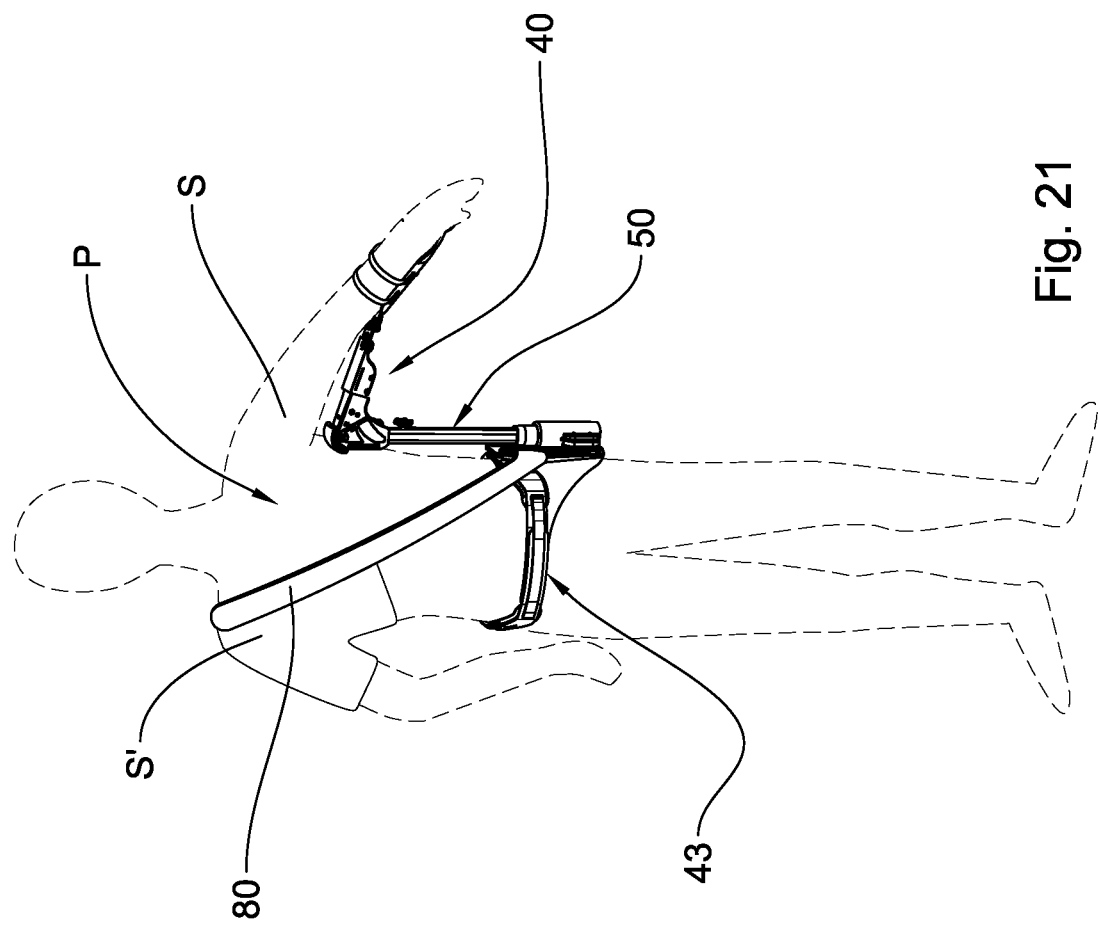

FIGS. 18-20 are views similar to FIGS. 14-16 respectively but suggesting splint rotation; and FIG. 21 is an elevational view of a patient illustrated in phantom lines being operatively fitted with the supporting waist belt, orthosis upright column member and injured splint and uninjured arm shoulder strap from the embodiment of FIG. 11, showing that the upright telescopic column member extends generally closely spacedly parallel to the patient's torso, wherein no sector-shape gap is formed therebetween.

DETAILED DESCRIPTION OF THE EMBODIMENTS OF THE INVENTION

Figure 1:
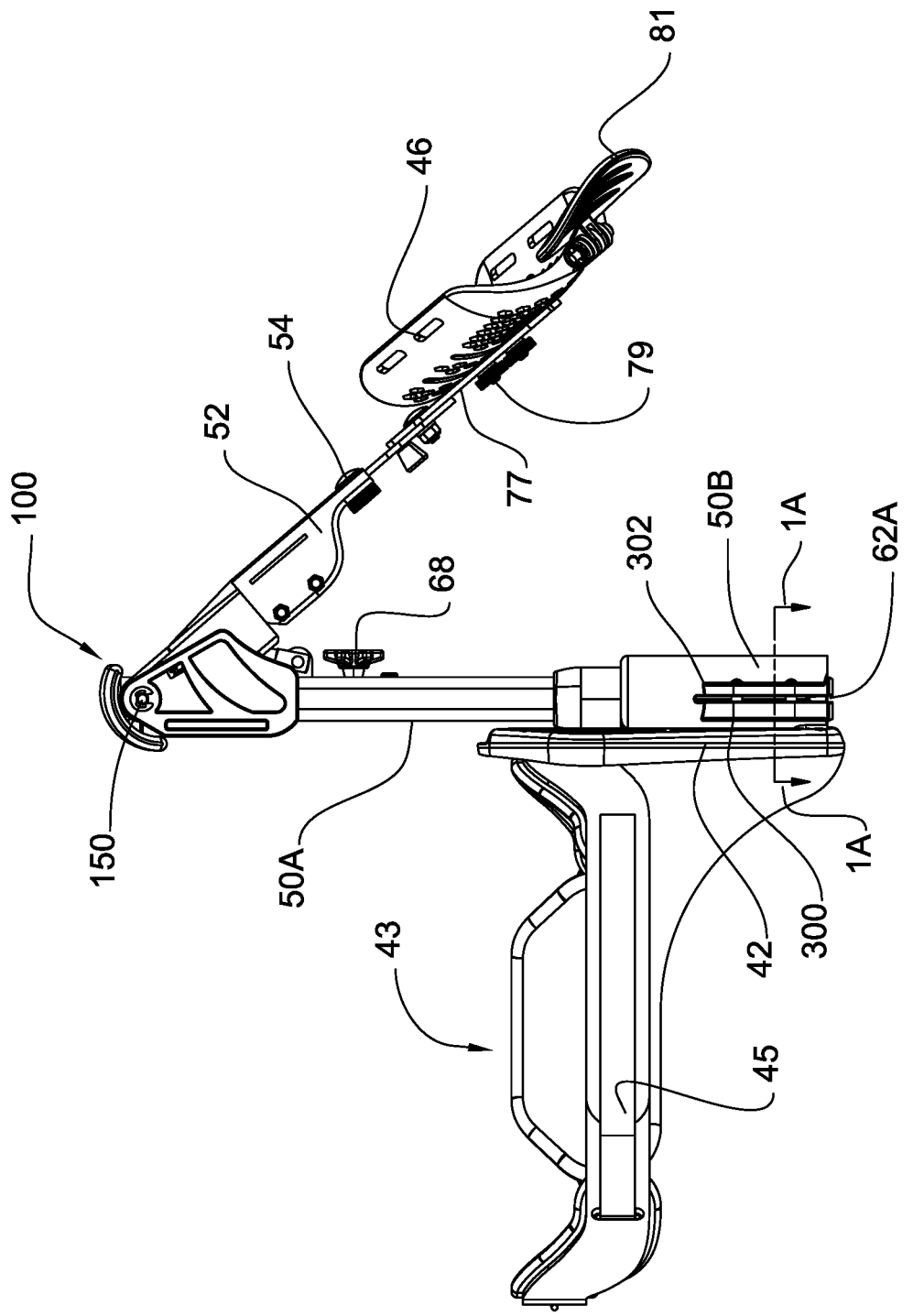
FIG. 1 is a side elevational view of an embodiment of orthosis and associated waist-supporting belt according to the invention.
Figure 1A:
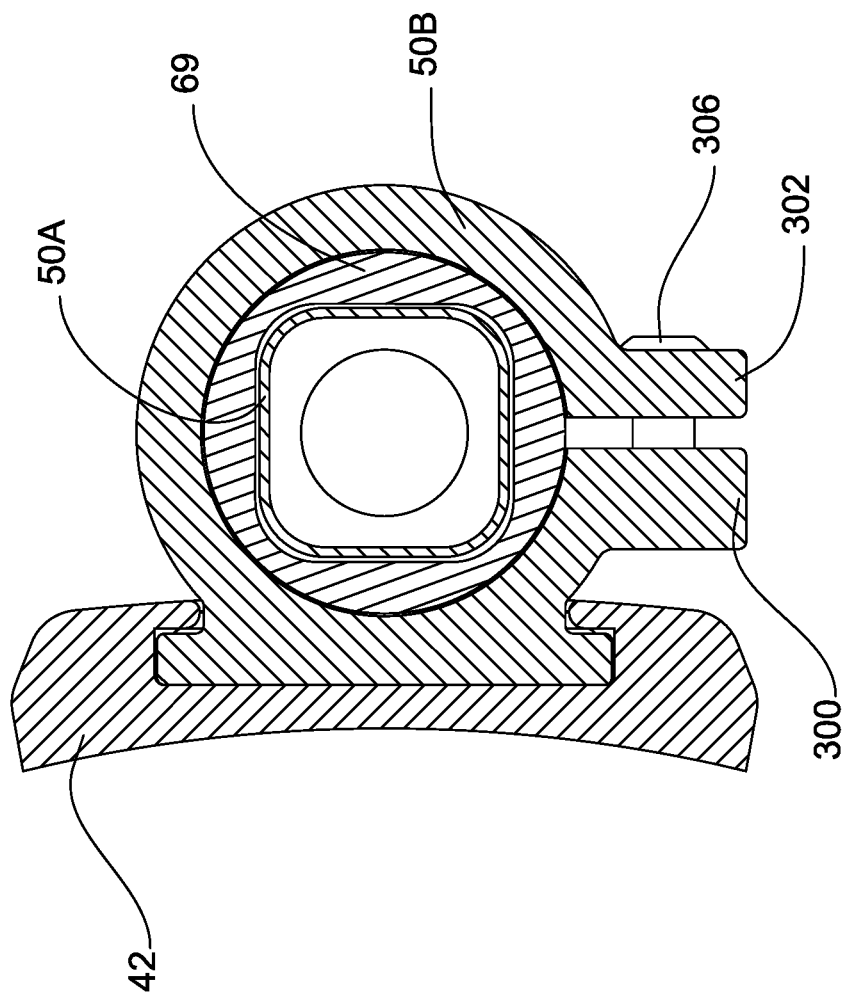
FIG. 1A is a cross-sectional view at an enlarged scale along line 1A-1A of FIG. 1, showing the two frictional locking plates releasably lockable by the pair of tightening screws to releasably interlock against relative rotation the two coaxially mounted bottom tubular members of the upright column member.
Figure 2:
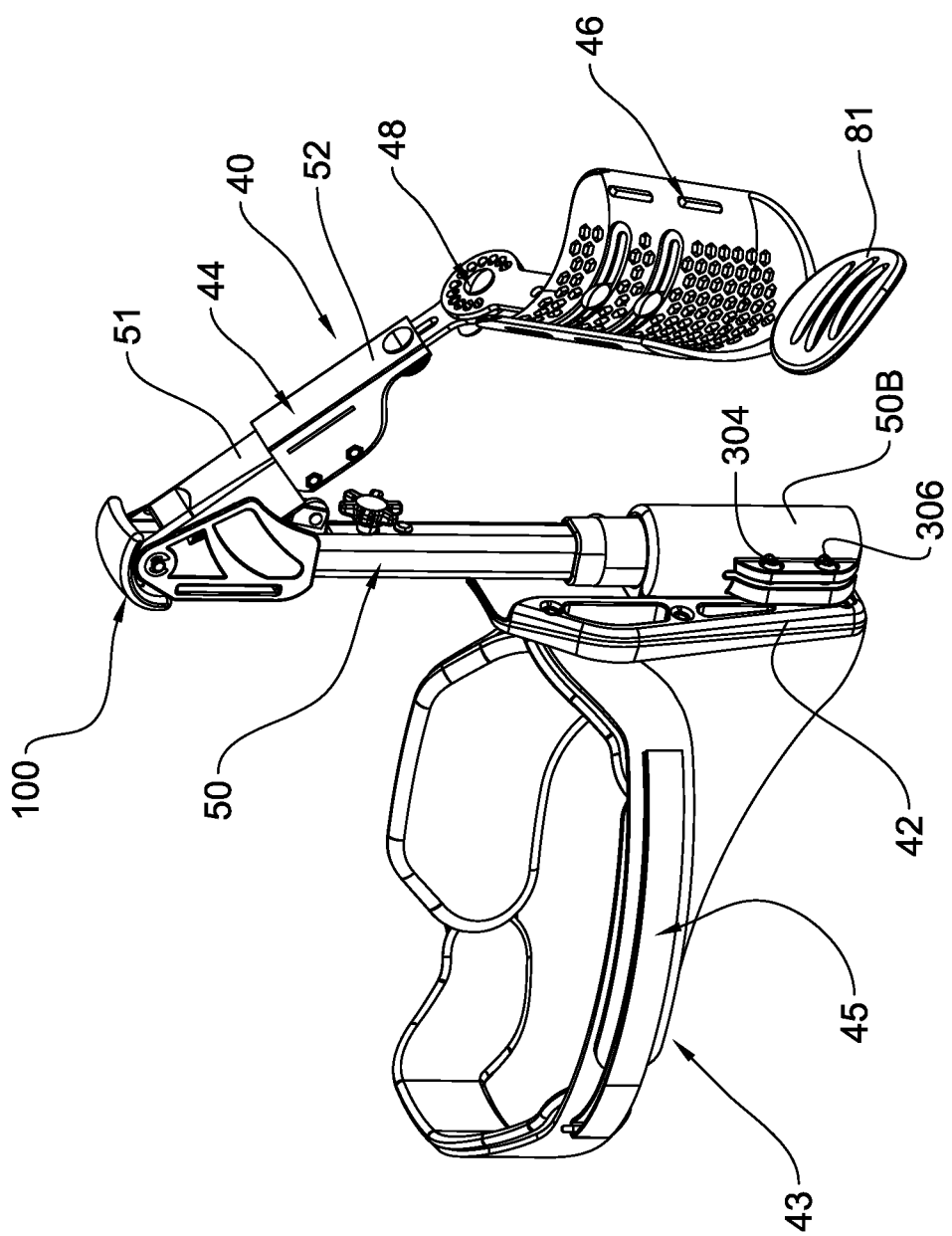
FIGS. 2 and 3 are downwardly looking isometric views from two opposite lateral sides of the orthosis from FIG. 1.
Figure 7:
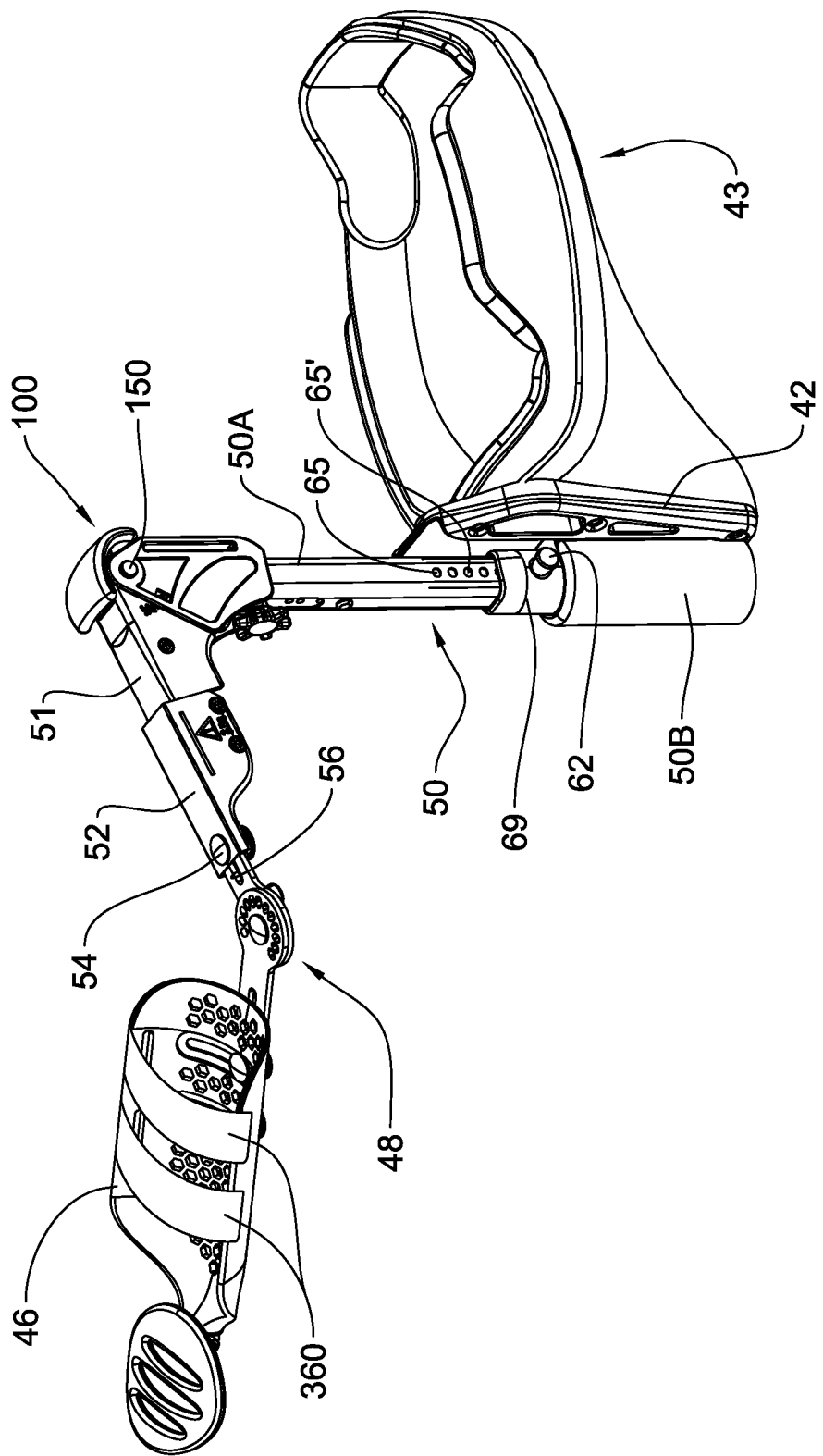
Figure 8:
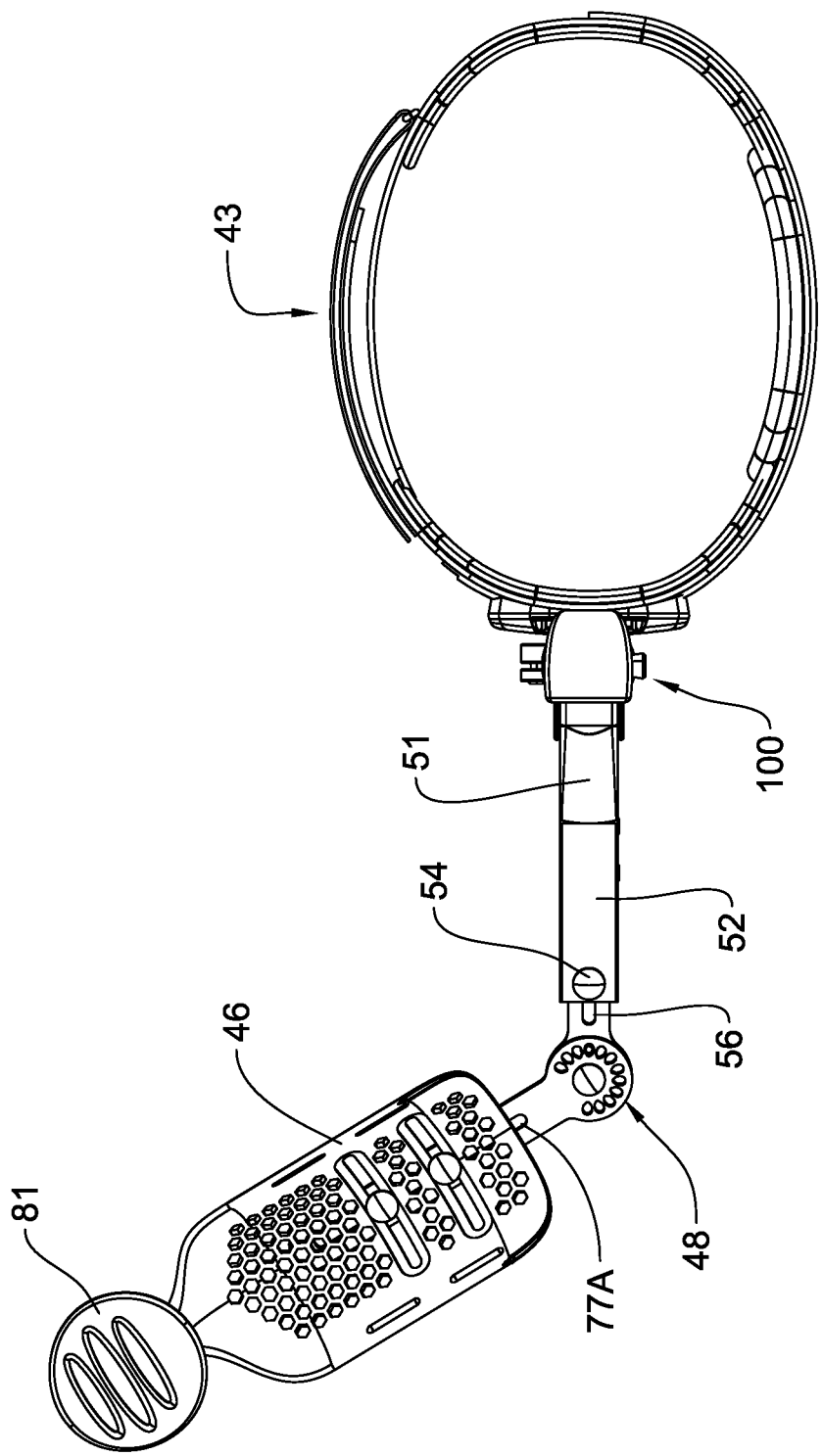
Figure 9:
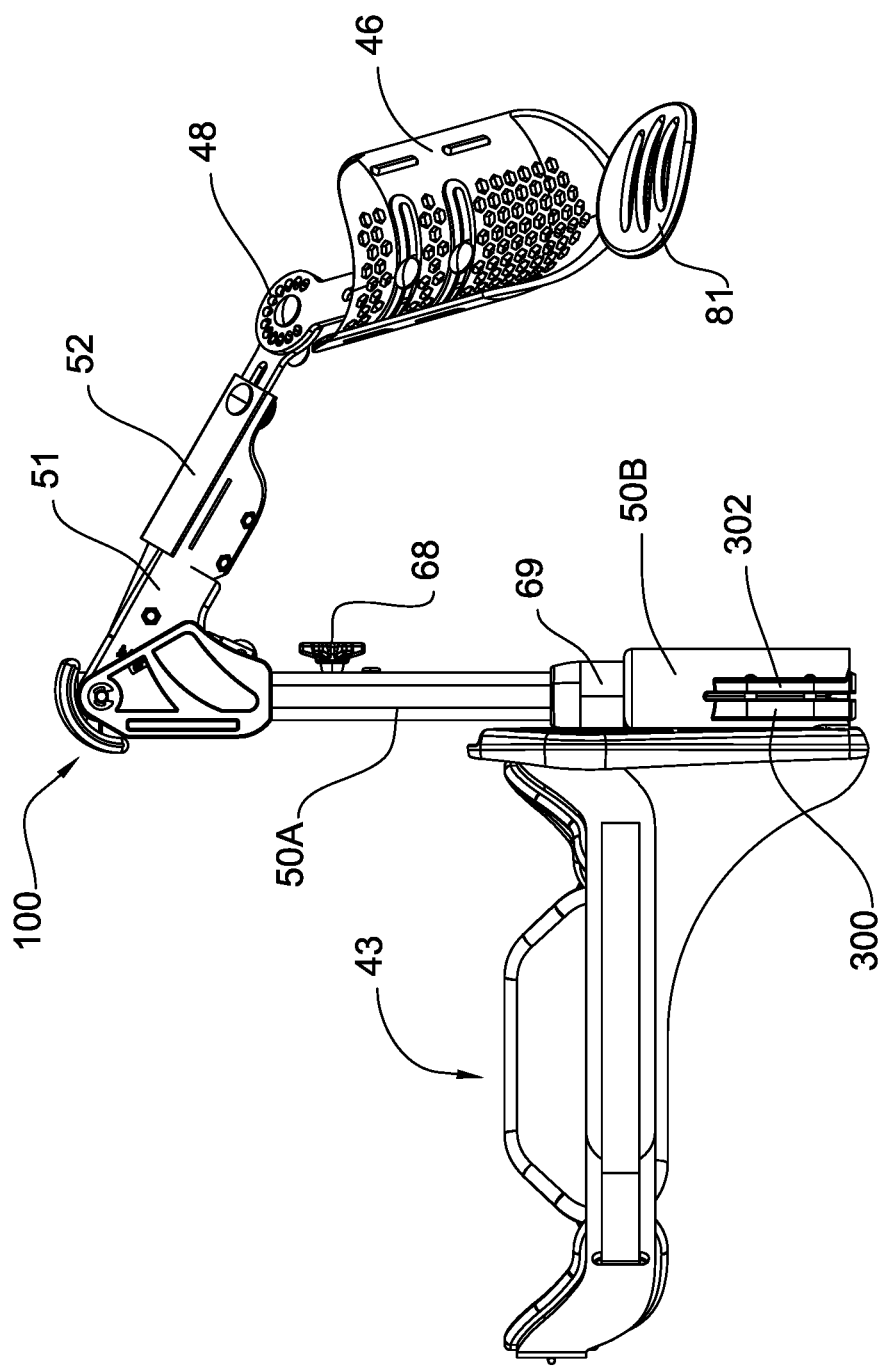
FIGS. 9 and 10 are view similar to FIGS. 1-2 respectively, but suggesting rotation of the splint cradle.
Figure 10:
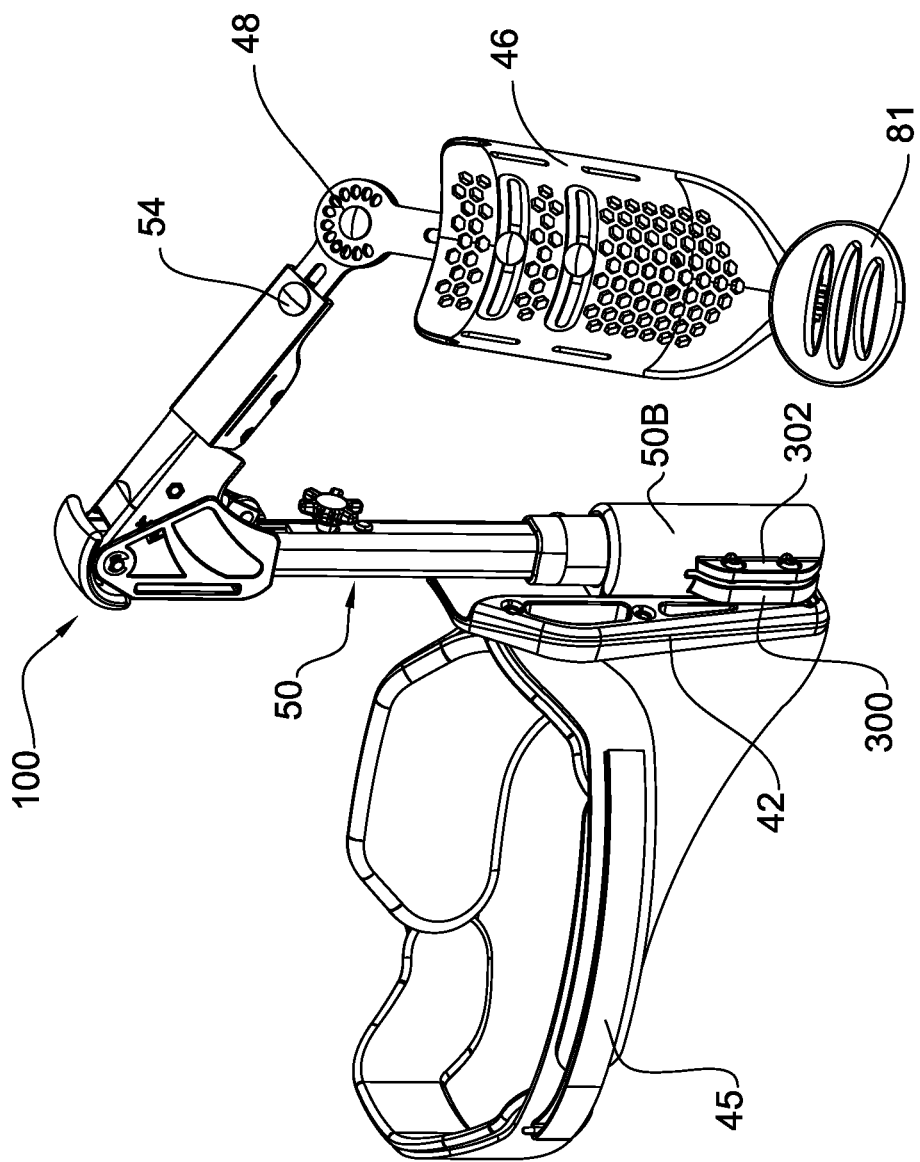

As seen in the drawings, e.g. FIGS. 1-2 and 7, the orthosis 40 includes an anchor plate 42 for attachment to a waistband belt member 43 around the waist of a patient, a forearm rigid support member or splint 44, a cradle member 46 carried at an outer end of splint 44 by a mounting means 48 for relative movement thereabout, an upright connector or column member 50 connecting at its top end portion thereof to the inner end portion of splint main body 44 about pivot mount 100, and at its bottom end portion to anchor plate 42. The splint 44 forms a cantilever with the upright column member 50.

In one embodiment, mounting means 48 forms an elbow joint, providing continuous elbow mobility in angularly variable condition ranging e.g. between 30° and 165° as an unlocked joint, and locking capabilities at various positions e.g. in 25° increments.

Figure 5:
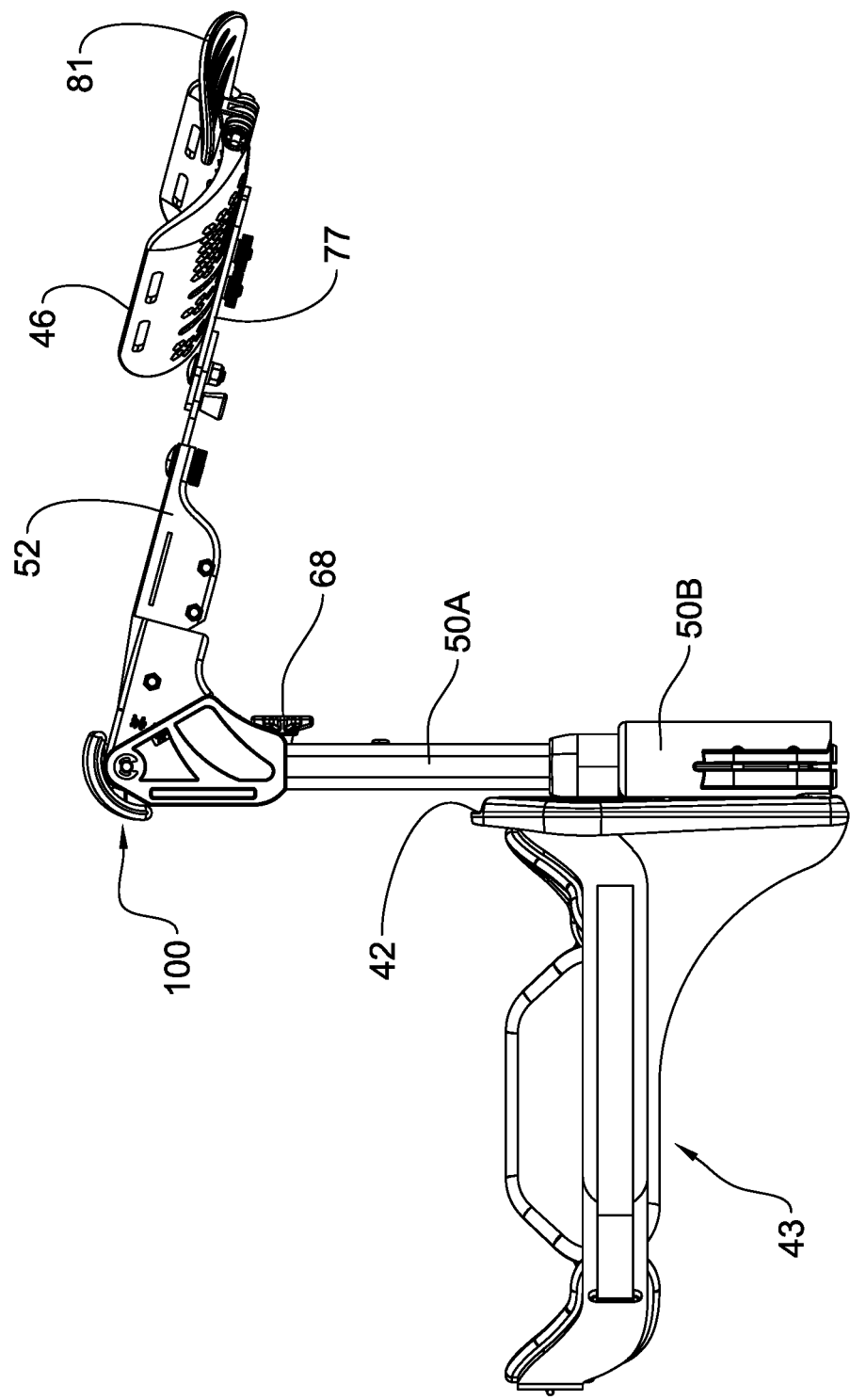
Figure 5A:
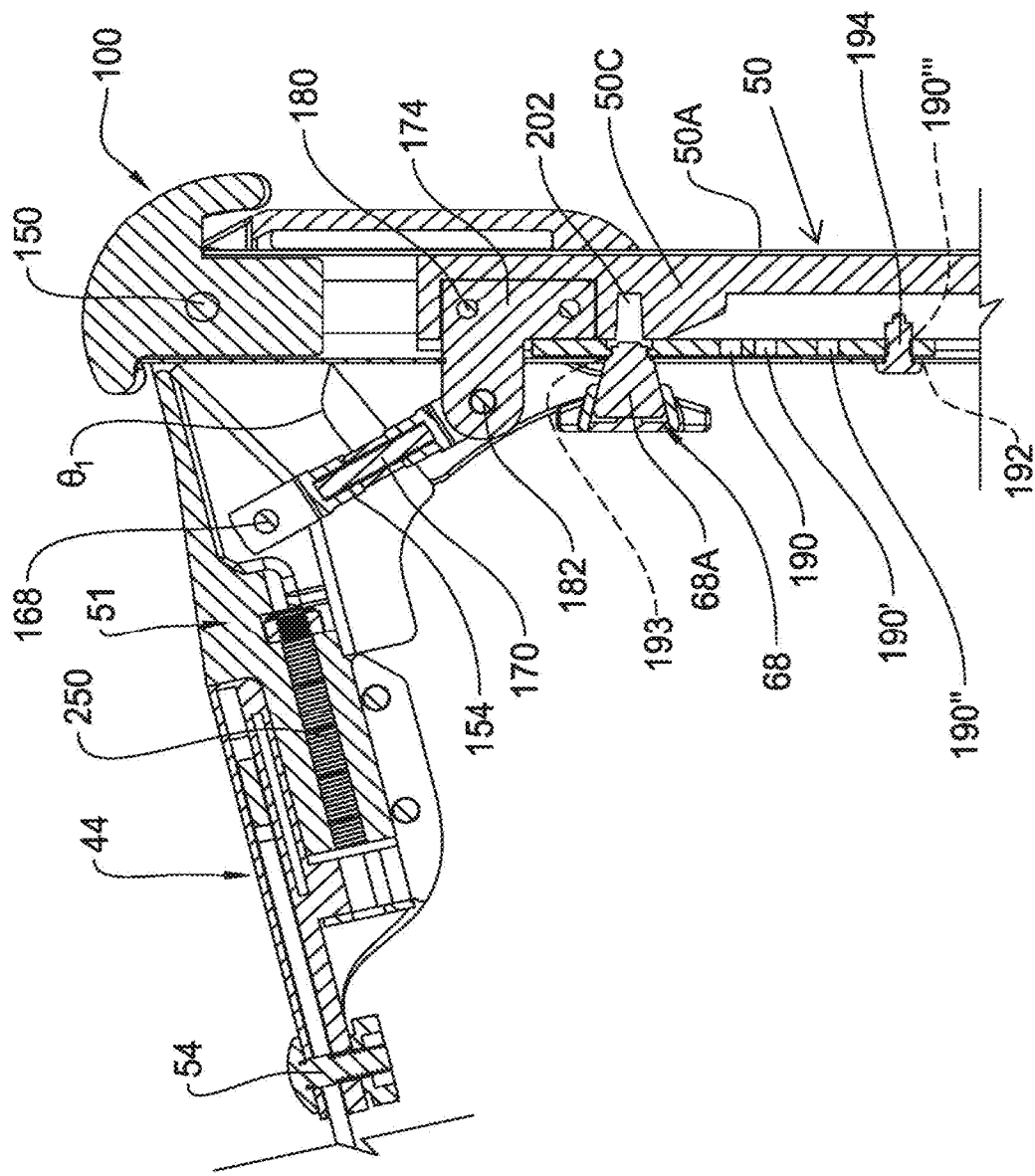
FIG. 5A is an enlarged sectional view of the upper portion of column member and adjacent inner portion of support splint from a perspective rotated half a turn relative to that of FIG. 5, and also showing the spring-loaded twist activated plunger in its retracted condition.
Figure 5B:
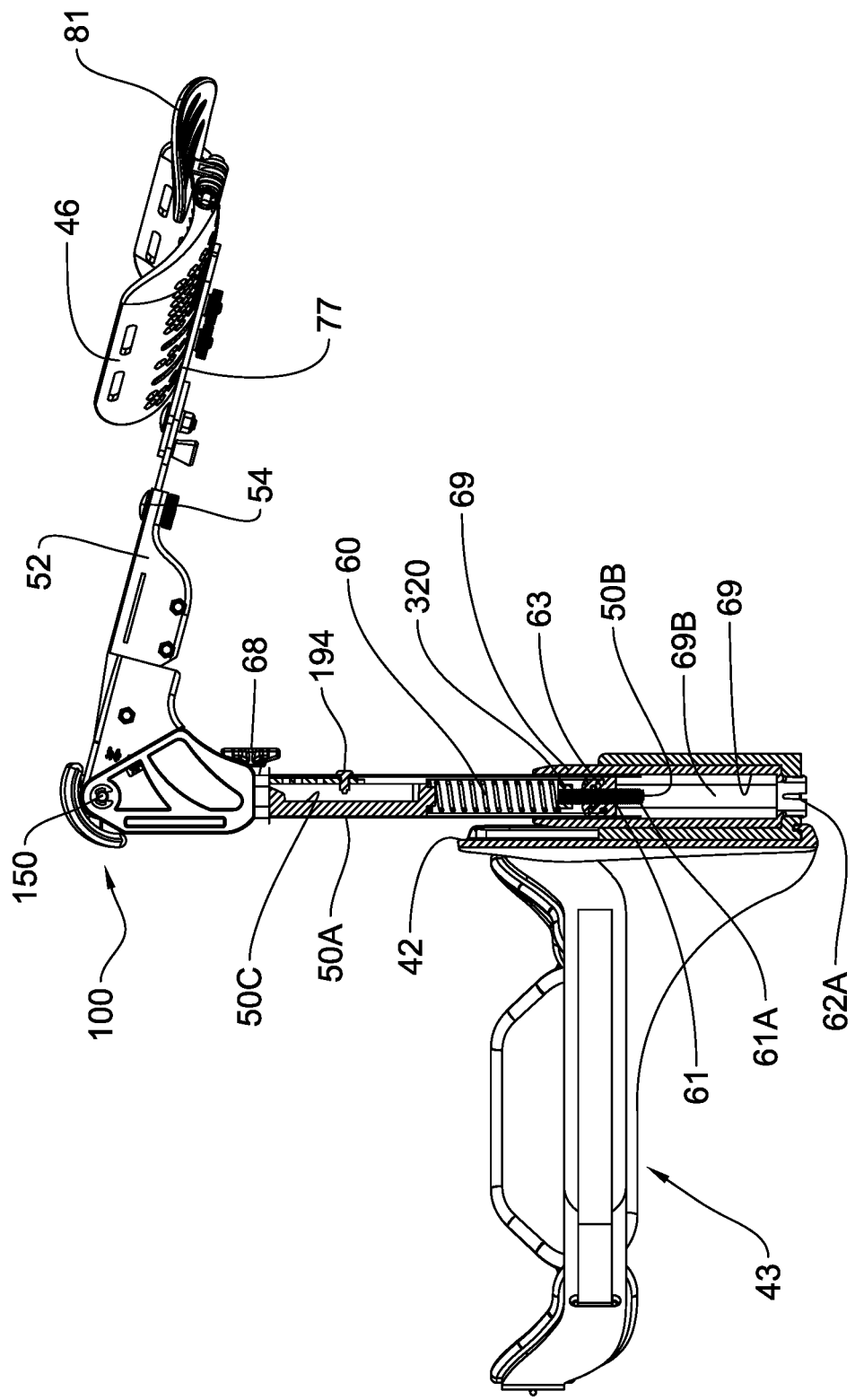
FIG. 5B is a view similar to FIG. 5 but with the column member in sectional view.

With further reference to FIGS. 5A, 5B and 7, the splint cantilever carries the patient's arm load to the column member 50 where it is forced against by moment and shear stress, allowing the splint 44 and supported patient's arm to overhang, however without external oblique bracing load as was the case with prior art U.S. Pat. No. 9,204,989. Thus, the patient's injured arm elbow clears the supporting column member 50.

In one embodiment, the splint 44 consists of two telescopic segments 51 and 52, wherein a bolt 54 transversely extends through female splint segment 52 and releasably lockingly engages an ovoidal slot 56 extending lengthwisely of male splint segment 51.

Figure 13:
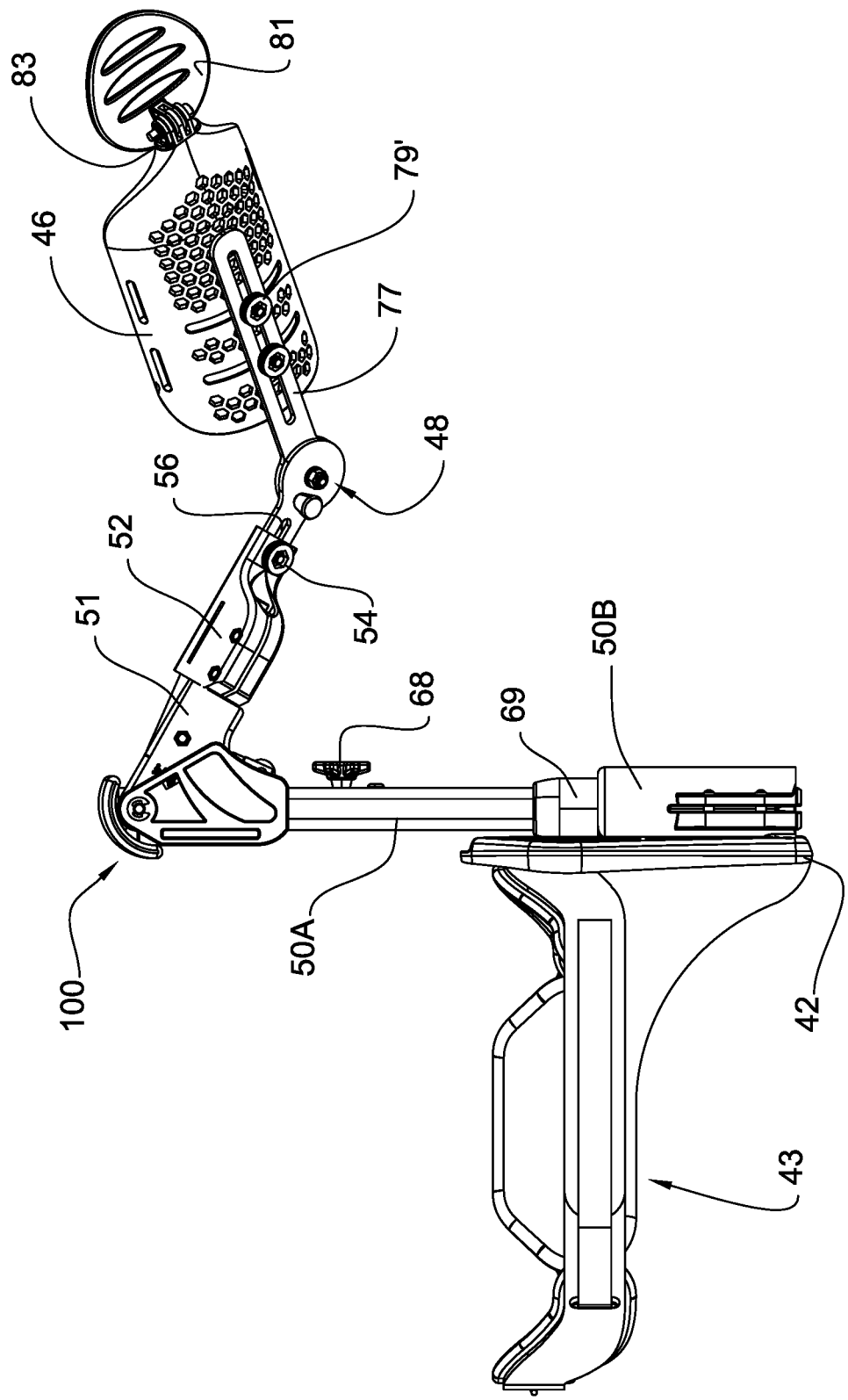
FIG. 13 is a view similar to FIG. 1 but with the cradle splint further rotated.
Figure 13A:
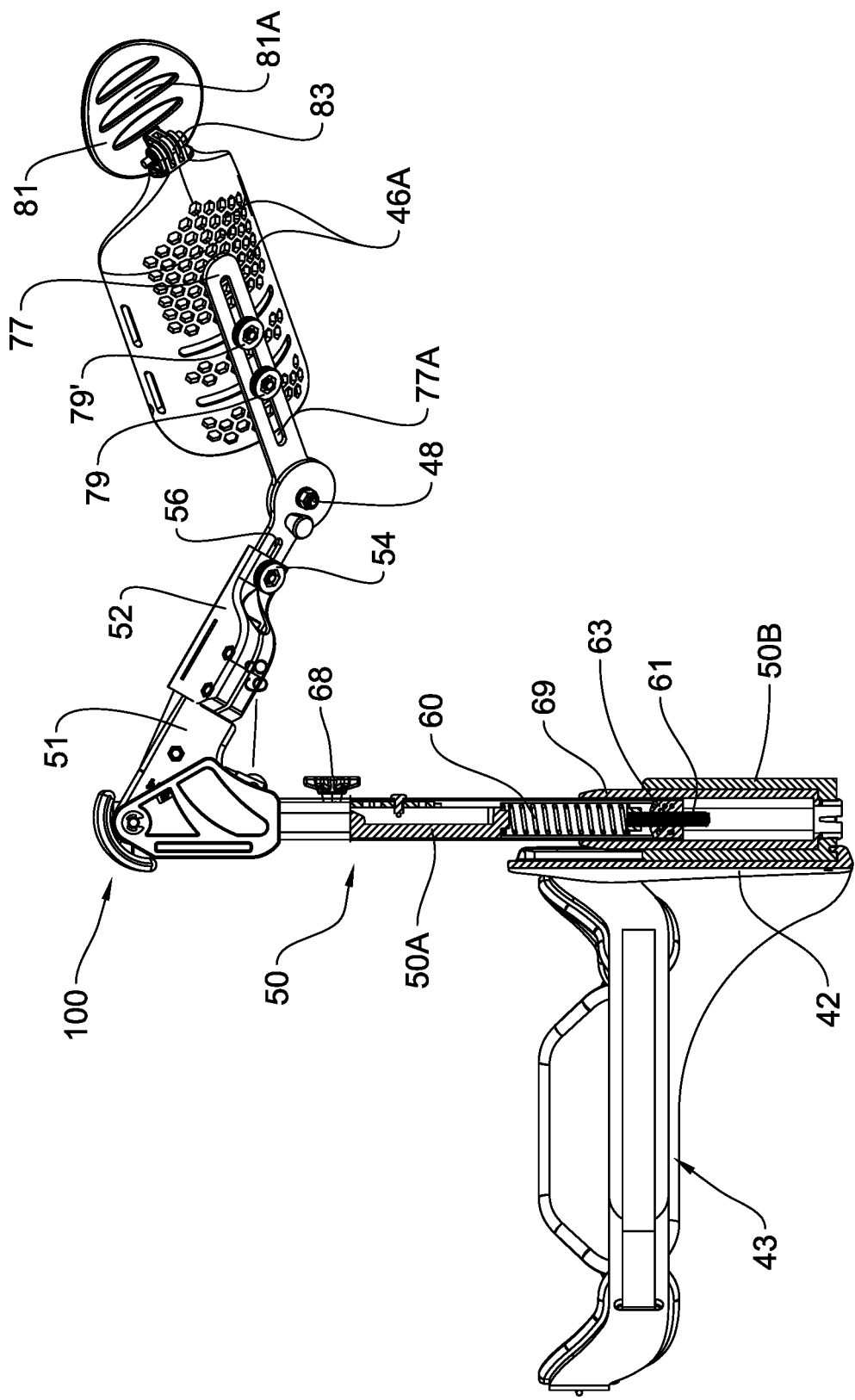
FIG. 13A is a view similar to FIG. 13 but with the upright telescopic column member shown in sectional view.
Figure 13B:
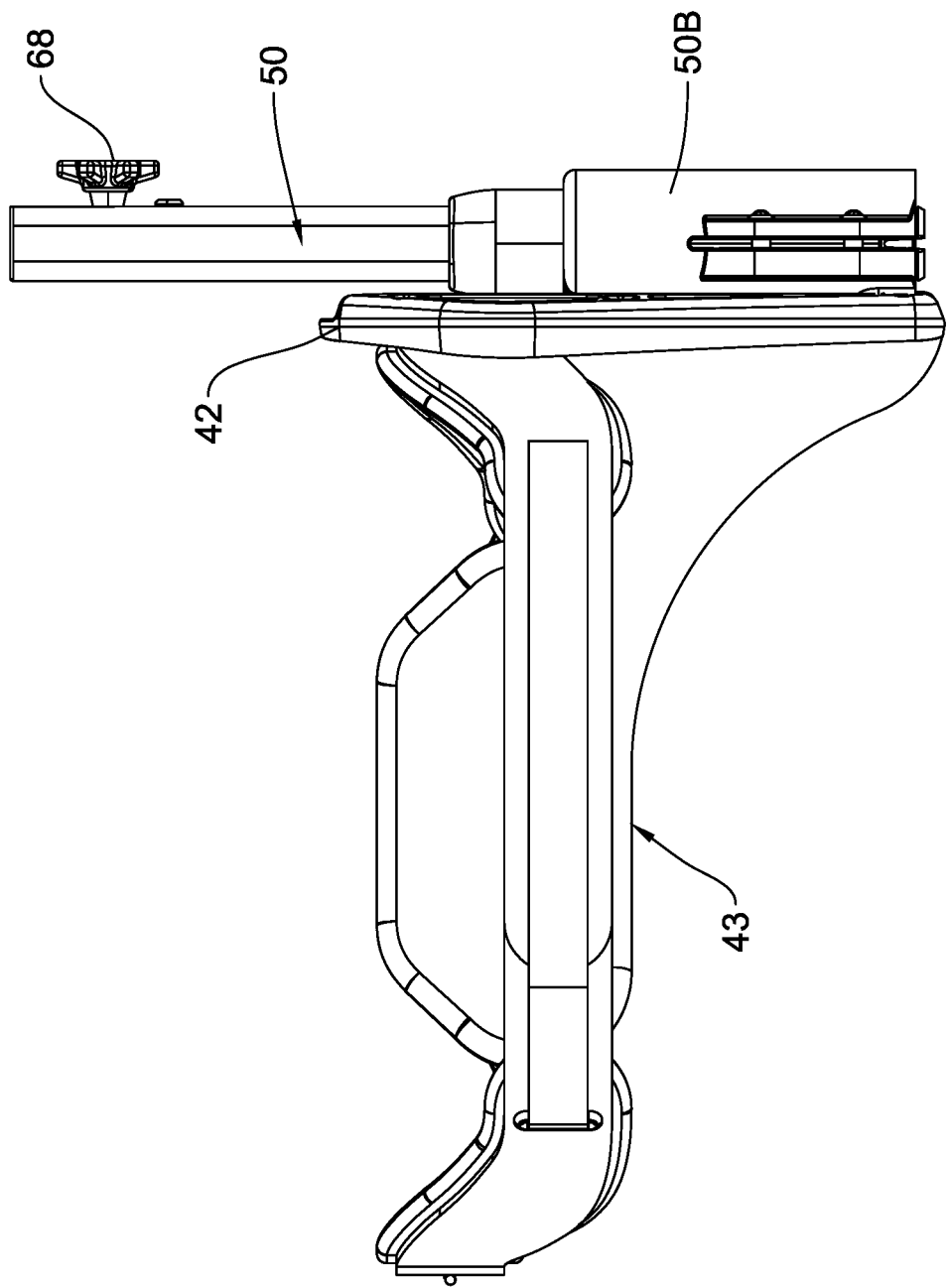
FIG. 13B is an enlarged view of the upright telescopic column member and waist belt from FIG. 13.
Figure 17:
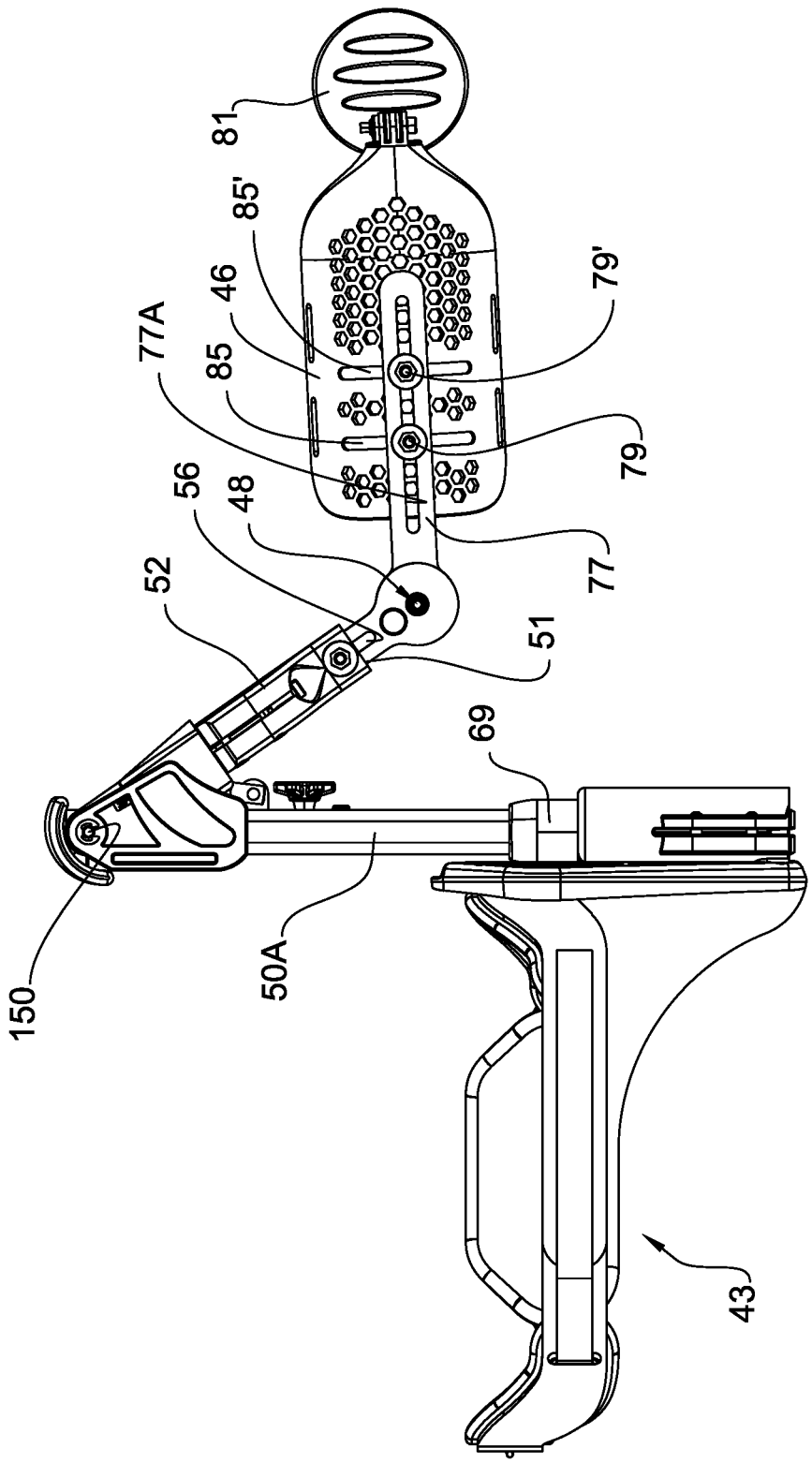
FIG. 17 is a view similar to FIG. 1 but with the relative splint positioning of FIG. 14.

In the embodiment shown e.g. at FIGS. 13 and 13A and 17, mounting means 48 forms a pivot mount pivotally interconnecting splint segment 51 to one end of an elongated generally rectangular carrier 77 e.g. with rounded corners as shown. Carrier 77 defines an elongated ovoidal slot 77A through which extends a few slider bolts 79, 79', which slidingly releasably lockingly interconnect cradle member 46 and carrier 77 transversely thereof. Slider bolts 79, 79', and elongated carrier 77 therefore provide telescopic extension/retraction motion capability of cradle member 46 relative to splint main body 40. Cradle member 46 may further include a number of moisture venting bores 46A. A handle rest member 81 may be carried at the outer end of cradle member 46 opposite splint mounting means 48, by way of a joint member 83. Hand rest member 81 may also have moisture venting slits 81A.

In one embodiment best illustrated in FIGS. 13A and 17, a few (e.g. two) ovoidal slots 85, 85' are made in cradle 46 transversely of and opening into cradle member ovoidal lengthwise slot 77A, to provide transverse roll adjustment over and above the telescopic lengthwise adjustment capability for cradle member 46.

In one embodiment shown e.g. in FIG. 2, the width of waistbelt member 43 is adjustable by way of hook and loop fastener bands 45. Belt 43 may include breathable cushioning.

The technical improvements of the present invention thus include the following ingenious elements: bilateral use; stability and mobility of the orthosis; adding an articulation to the hip; and adjustment in the transverse plane.

As best shown in FIGS. 1A, 2, 9-10 and 13D, in one embodiment, tubular member 50 B is made from a resilient compressible nylon material and defines a slit 290 made lengthwisely of a lower lateral wall portion thereof. On opposite sides of slit 290 are carried radially outward frictional interlock plates 300, 302, spaced by a gap 292. Each transverse plate 300, 302, includes a pair of transversely registering threaded bores 293, 294 and 295 and 296 respectively, wherein registering bores 293 and 294 are threadingly engaged by first tightening screw 304 and registering bores 295 and 296 are engaged by second tightening screw 306. When screws 304 and 306 are released, tubular elements 50A and 69 become free to rotate about stationary tubular base 50 B; whereas when screws 304 and 306 are tightened, plates 300 and 302 are brought toward one another wherein gap 292 diminishes in width and tubular members 50B and 69 frictionally interlock with one another thus interlocking tubular elements 50B, 69 and 50A.

Figure 11A:
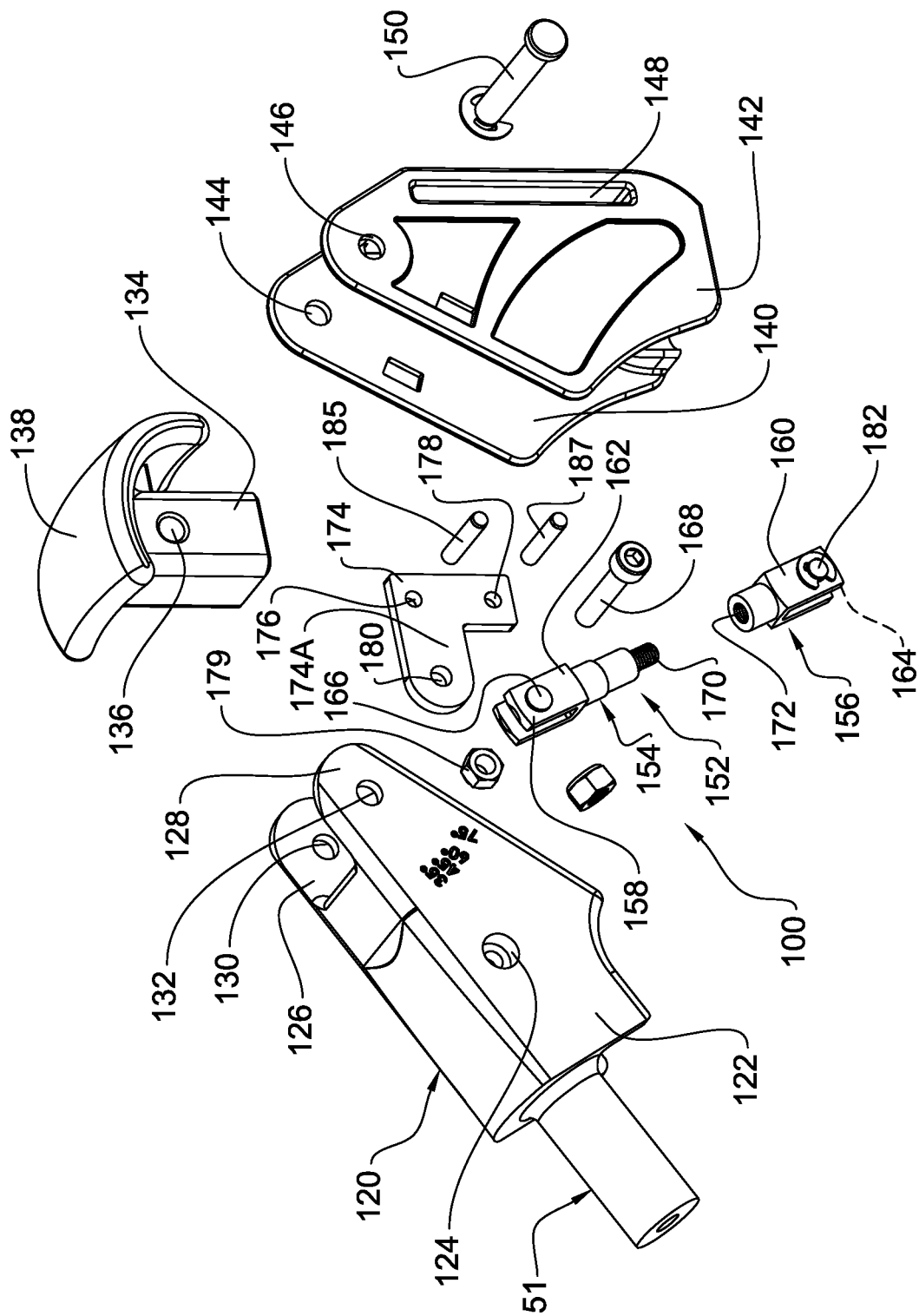
FIG. 11A is an enlarged exploded view of the intermediate arm joint between the splint and telescopic column member.
Figure 11B:
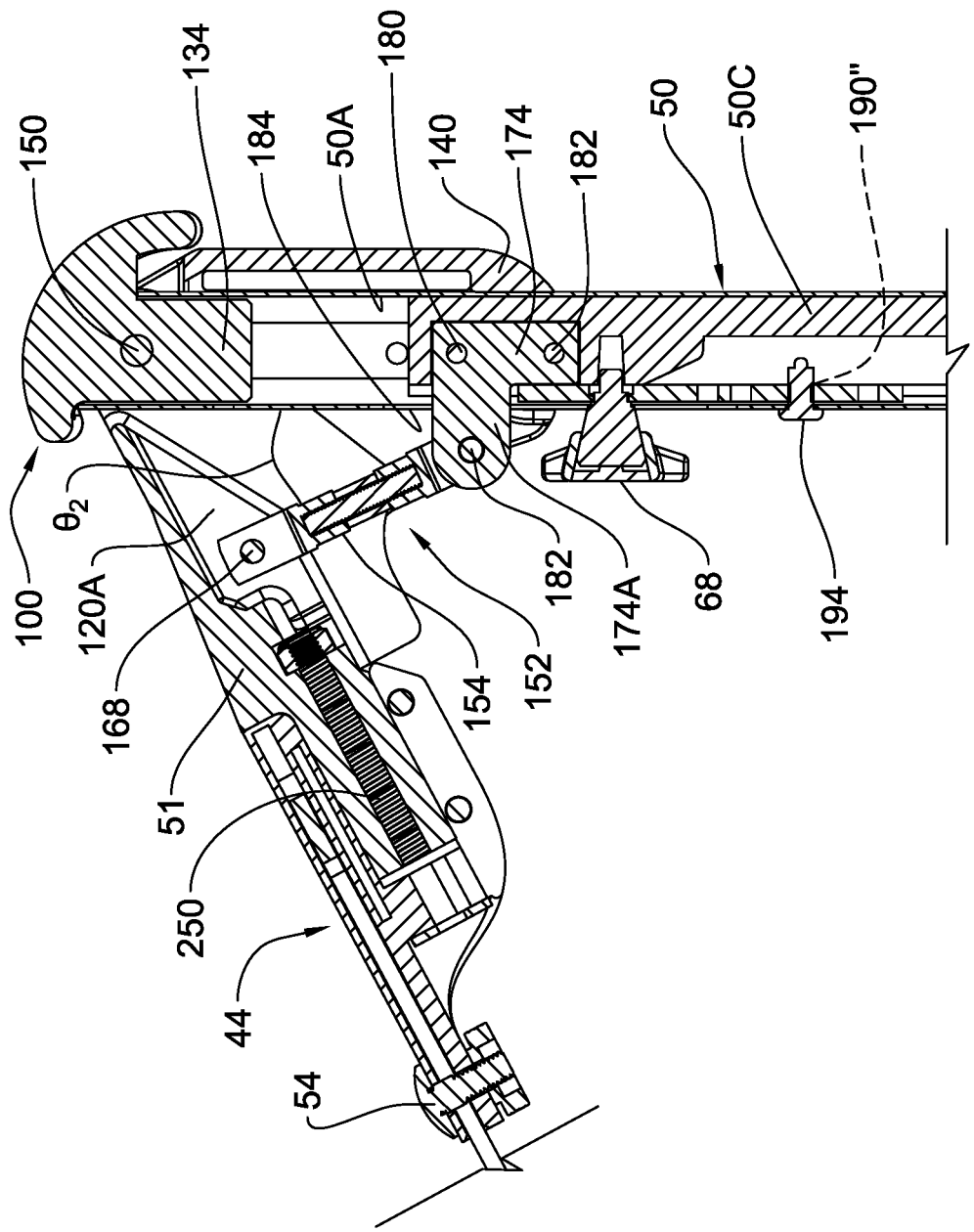
FIG. 11B is a view similar to FIG. 5A but according to the relative support splint angular orientation shown in in FIG. 11.
Figure 12:
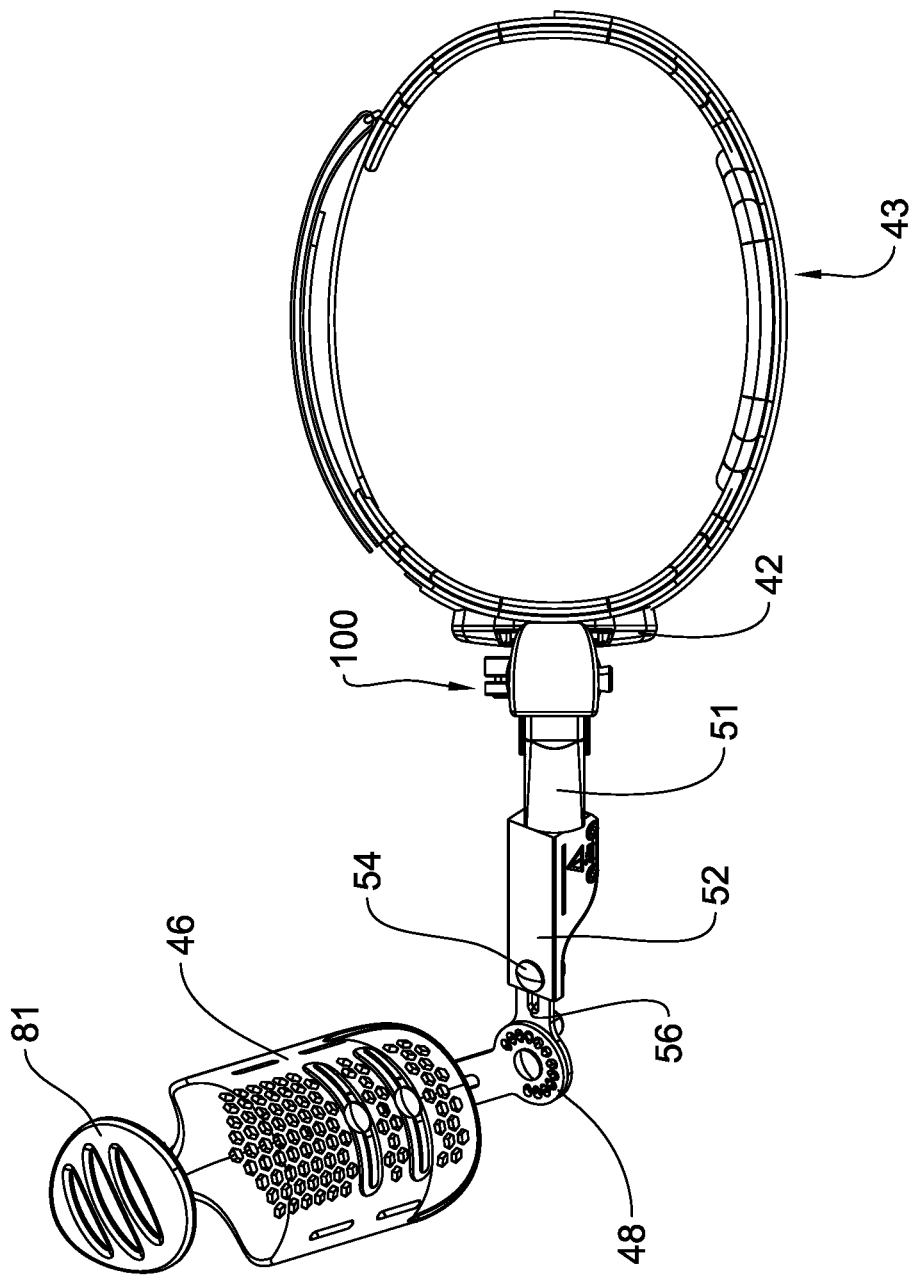
FIG. 12 is a view similar to FIG. 4 but with the cradle splint rotated.

As can be seen in FIG. 11B of the drawings according to the invention, there is added a shoulder joint 100. This joint 100 results in stabilization by attachment to the patient's injured arm in addition to the patient's coextensive forearm, continuous adjustment from 0° to 90° in the sagittal plane (internal-external rotation) with locking, and incremental adjustment in the frontal plane to fixed (discrete) angles selected for example between 30°, 35°, 45°, 60° and/or 75°.

As best illustrated in FIGS. 5A, 5B, 11B and 17A, in one embodiment, telescopic splint elements 51 and 52 each have a cross-sectional U-shape main body are further interconnected by a fixed screw 250 anchored at one end to inner splint element 51 by arcuate integral bracket 252 and at its opposite end to outer splint element 52 by transverse integral bracket 254. Screw 250 provides dampening means when splint elements 51 and 52 are rotated.

Splint elements 51 and 52 provide external and internal rotation capability of the shoulder adjustment to precise the position of immobilization, depending on the type of surgery.

Figure 3:
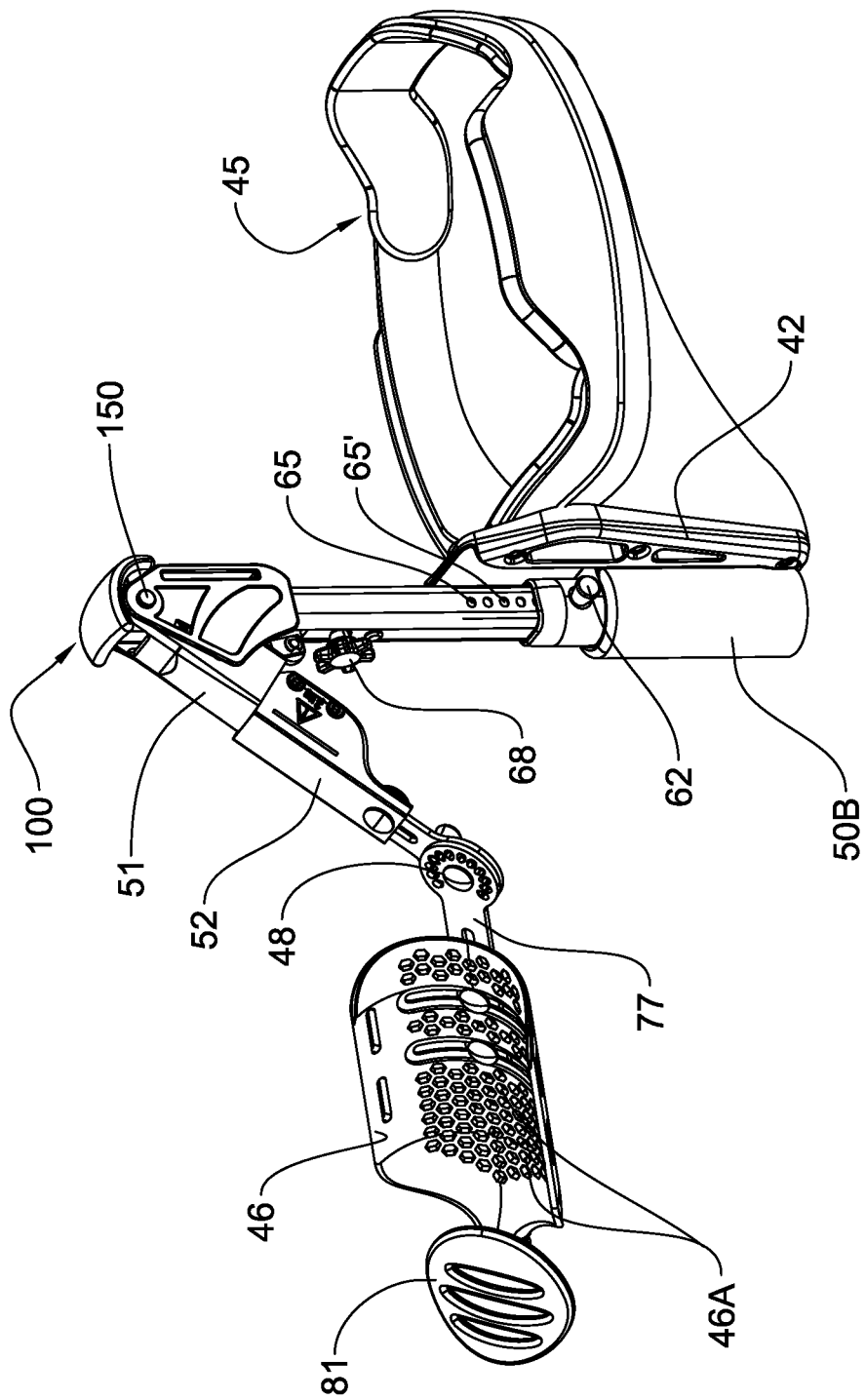
Figure 4:
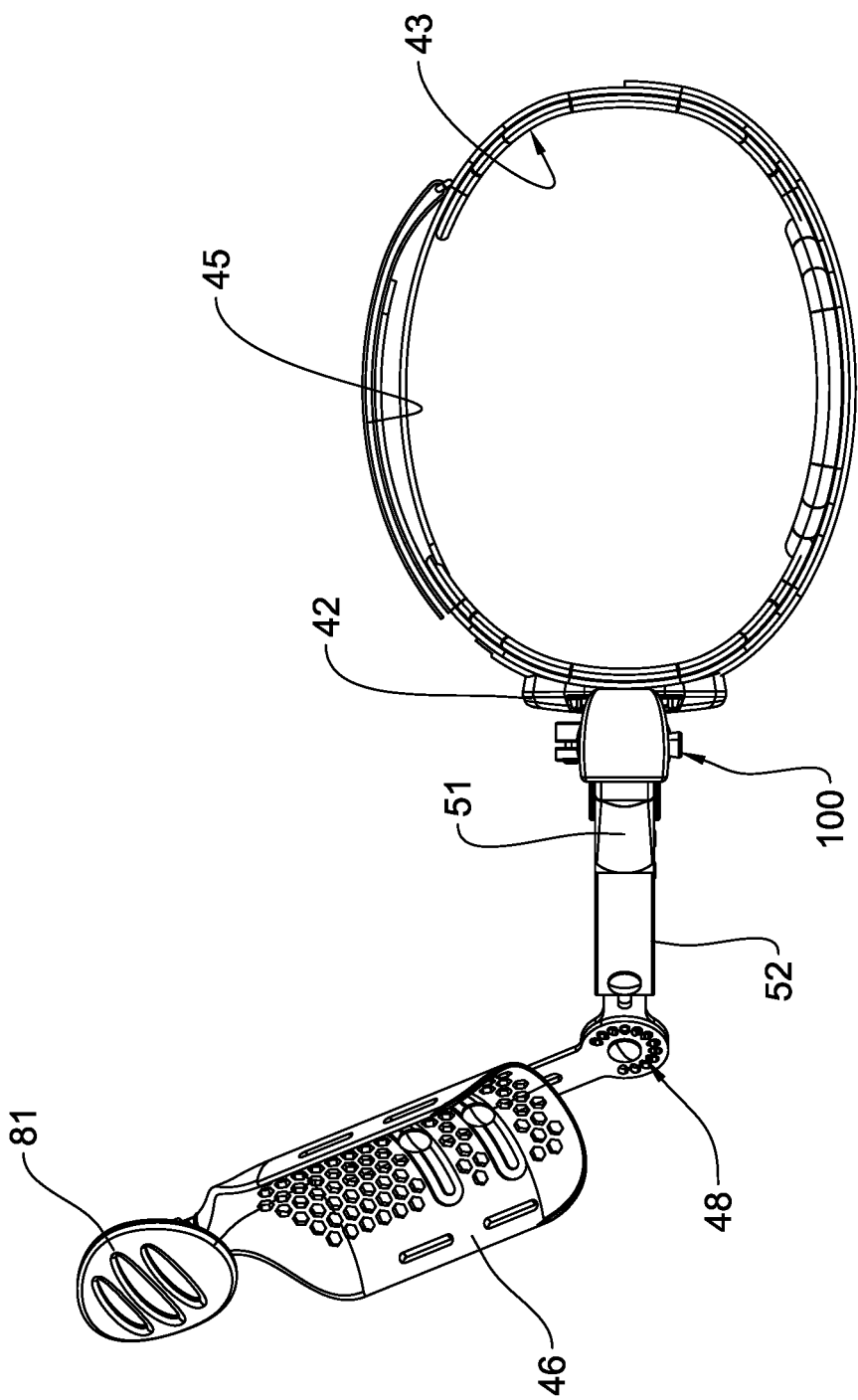
FIG. 4 is a bottom end view of the orthosis of FIG. 1.
Figure 13C:
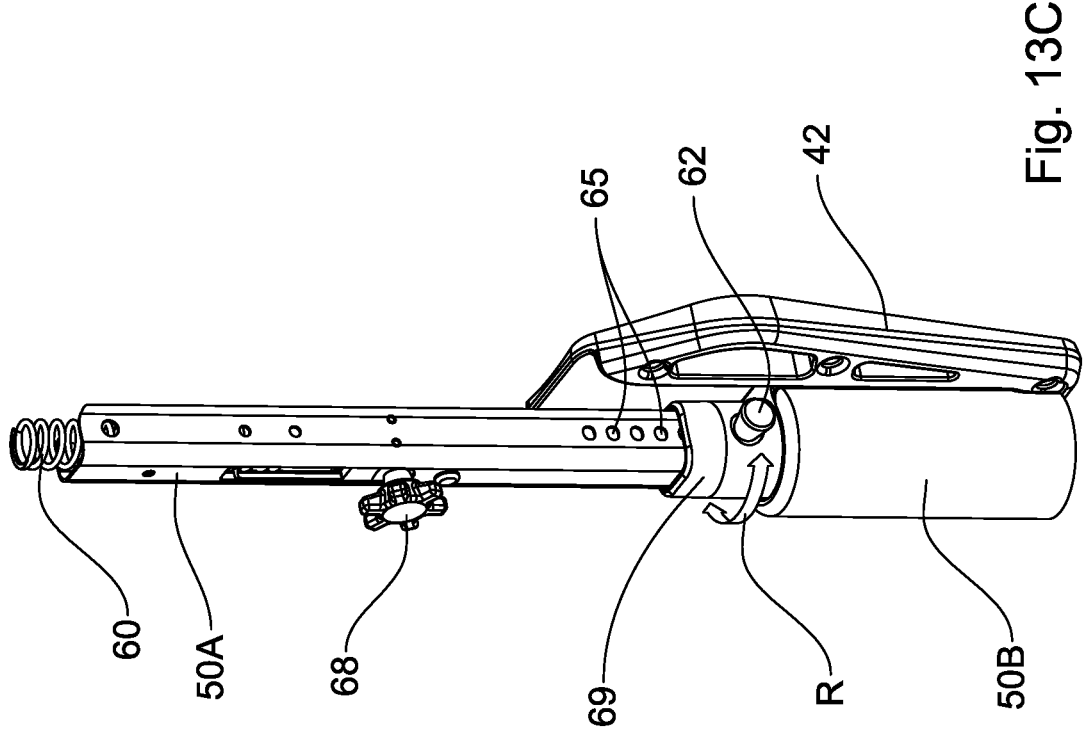
FIG. 13C is an isometric view of the upright column from FIG. 13B, and with the arcuate arrow band suggesting rotational capability thereof.
Figure 13D:
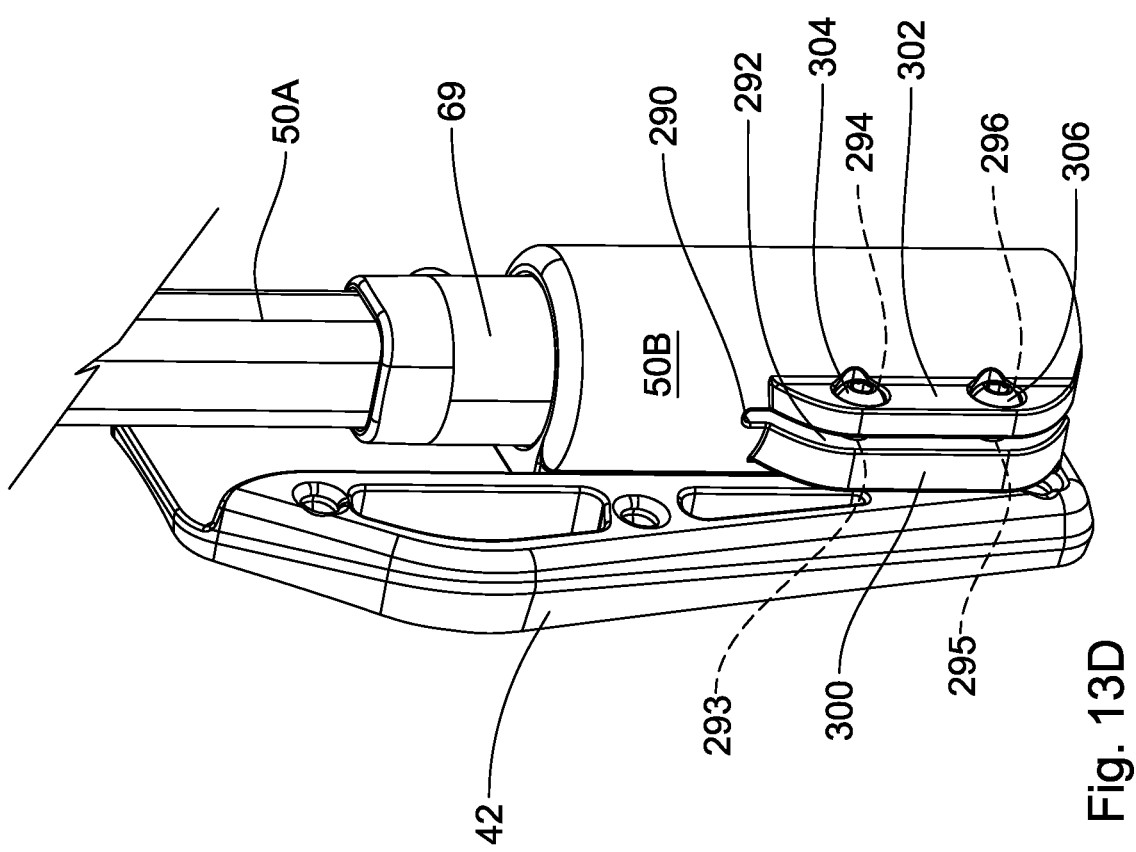
FIG. 13D is a still enlarged isometric view of the lower section of upright column member from another perspective relative to FIG. 13C.

The hip-shoulder upright column member 50 is characterized in that it extends generally parallel and closely spaced from the patient's torso. This upright hip-shoulder column member 50 has a telescopic length adjustment means which can be releasably locked at selected conditions. More particularly, and as best shown in FIGS. 3, 11 and 13C, this length adjustment means is embodied by the lower portion of column member tubular portion 50A including a number of lengthwisely spaced bores 65, any of which may be selectively engaged by screw member 62. By selecting one of bores 65, 65', . . . engaged by screw 62 therein, adjustment of telescopic extension of male tube 50A relative to female tube 69 and associated bottom base tube element 50B will be enabled, according to the height of the patient's torso. The external handle part of screw member 62 is fitted to enable manual adjustment control of spring tension for axial spring 60.

The splint member cradle may be perforated with multiple moisture venting perforations or bores 46A (see e.g. FIG. 13A) for accommodating patient's arm sweating/perspiration.

As illustrated in the embodiment of FIGS. 11, 11B and 13A, the column member 50 includes a lowermost base tubular element 50B, from which projects a rotatable tubular element carrying a +telescopic assembly comprising a male tubular member 50C and a female tubular member 50A. That is to say, column member female segment tubular member 50A is telescopic and defines an inner tubular segment 50C lengthwisely movable within the hollow of upper tubular segment 50A.

As best illustrated in FIGS. 5B, 5D, 7, 13A, 13C and 17B of the drawings, in one embodiment, an elongated compression coil spring 60 is coaxially mounted lengthwisely inside the hollow of column member telescopic female tubular member 50A, engaging at its top end male tubular member 50C and at its bottom end a cross-sectionally hexagonal rod or "internal chord" 61 carried by a seat 63 within the hollow of and integral to the upper portion of rotatable tubular member 69. The top end of rod 61 also carries a discoid seat 320 integral to the bottom end of coil spring 60. The bottom end of rod 61 forms a free end head 61A for releasable engagement by an Allen key W. Access to rod bolt head 61A by Allen key W is made possible via a bottom mouth 62A made at the bottom end of radially outward tubular members 50B and radially inward tubular member 69, and through the axial hollow 69B of inner tubular member 69. Upright internal chord 61 enables transmission of the patient's injured arm adduction movement on splint cradle 46, while axial coil spring 60 inside upright column member 50 provides resistance to patient's injured arm adduction on splint cradle 46.

As shown in in FIG. 13C, screw member 62 is carried by sleeve 69 rotatably mounted within stationary tubular base 50B. This is suggested by double arrow band R.

In the embodiment of FIGS. 11 and 21, a flexible sling band or strap 80 connects the waistband anchor section 42 to the patient's uninjured shoulder S' opposite the patient's injured shoulder S for patient P.

As illustrated in FIG. 21, the patient's uninjured shoulder S' may be covered with a short sleeve shirt section, whereby sling band 80 will abut thereagainst for patient's comfort and treatment compliance.

Figure 17A:
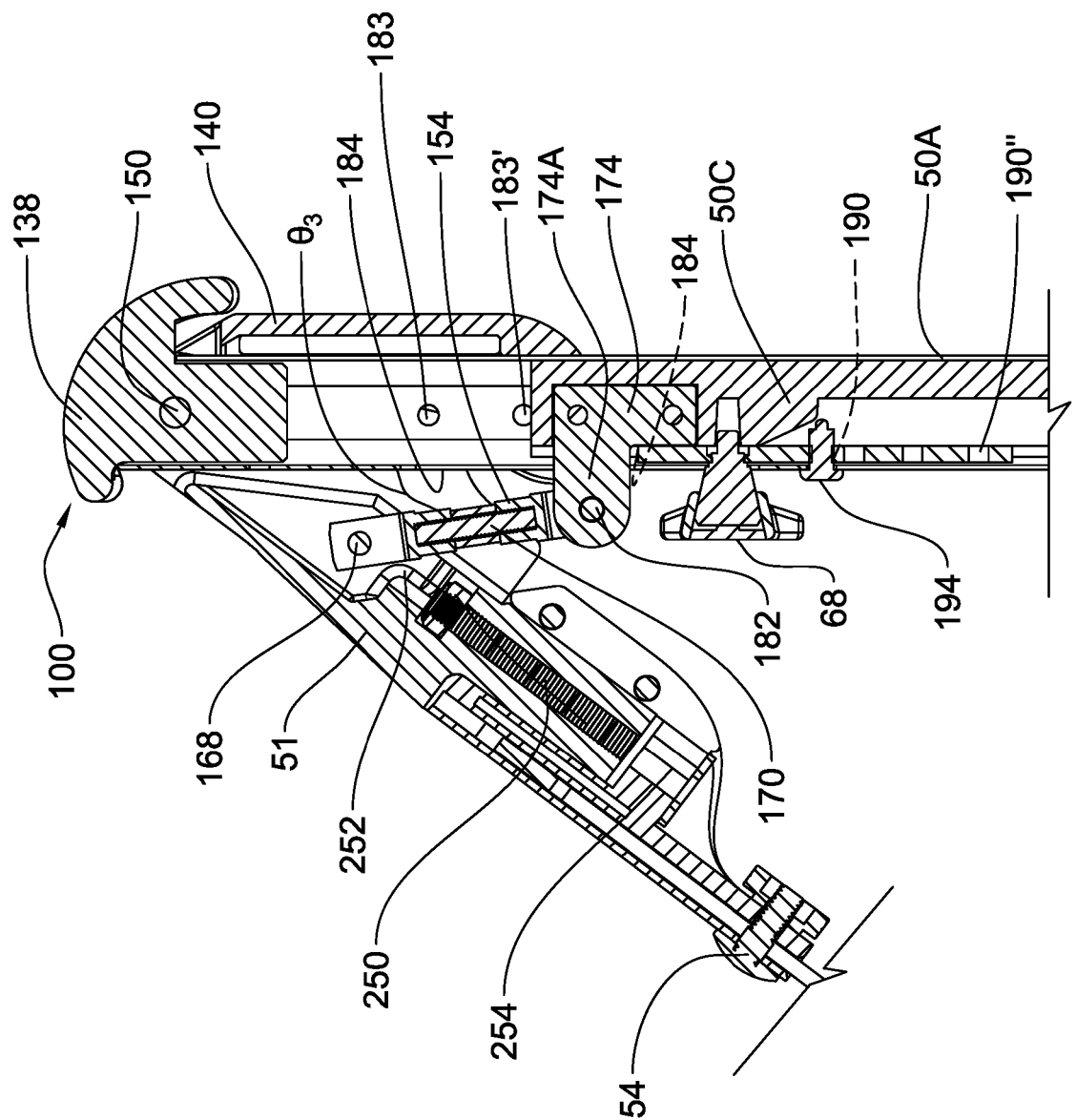
FIG. 17A is a view similar to FIGS. 5A and 5B but according to the relative support splint orientation of FIG. 17.
Figure 17B:
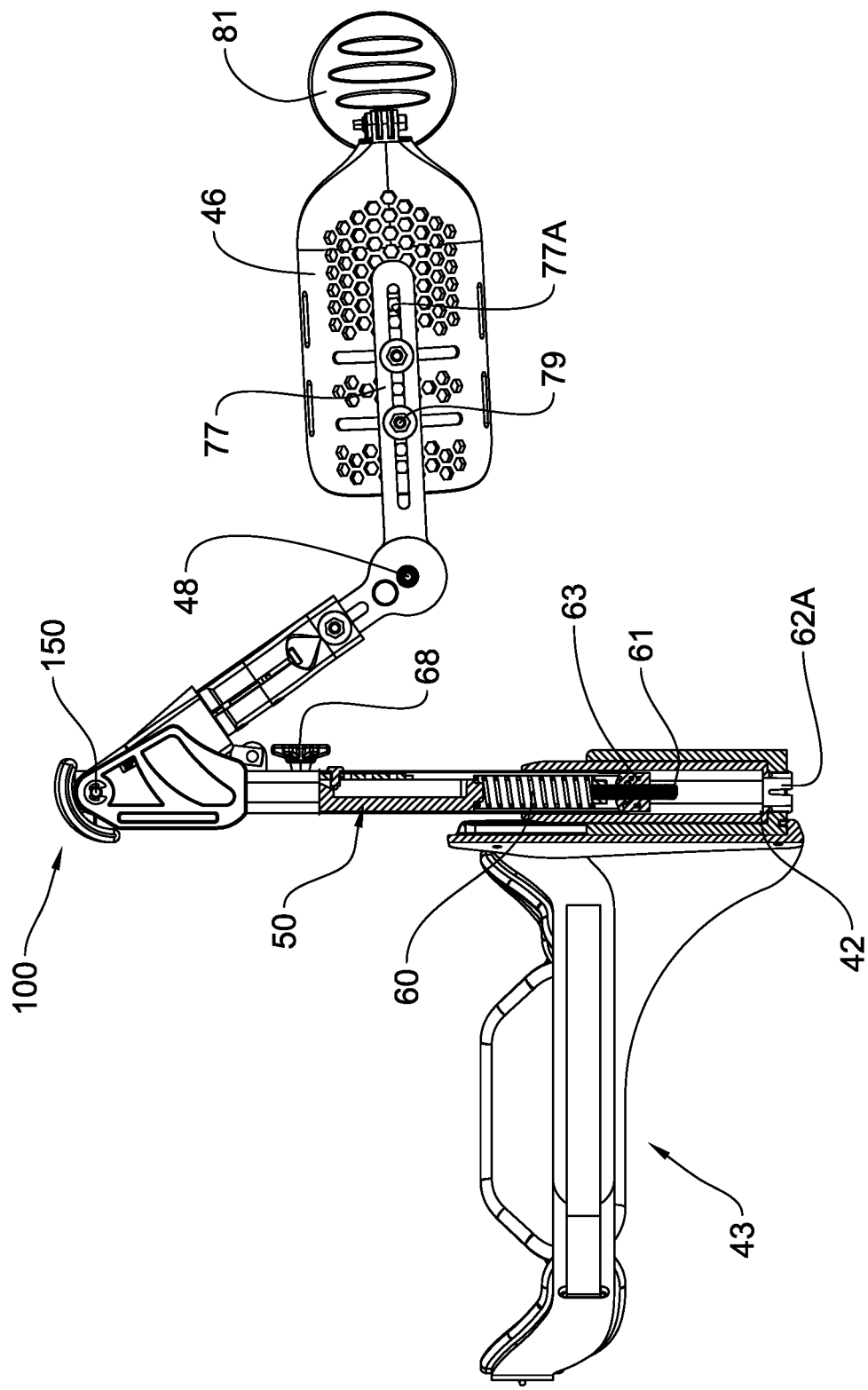
FIG. 17B is a view similar to FIG. 17 but with the column member in sectional view.

The sectional views in the orthosis embodiment of FIGS. 5A, 11B and 17A of the drawings, in combination with the exploded view of FIG. 11A, sequentially suggest how transverse splint member 44 pivots relative to upright column member 50. Splint inner segment 44 comprises an inner free end yoke section 120 defining a main body 122 with a first intermediate transverse bore 124, and two transversely spaced innermost ears 126 and 128 each having a corresponding bore 130 and 132 respectively in transverse register with one another. To the top end of upper tubular male element 50A of column 50 is fitted a tubular cap member 134 having a transverse bore 136. In one embodiment, the top end of cap member 134 is covered by an arcuate integral cover plate 138. Polygonal bracket plates 140, 142, are also provided, each including a top bore 144, 146, respectively and a vertical ovoidal slot 148. Bores 130, 132, 136, 144 and 146 are sized and shaped to accommodate therethrough a bolt 150 releasably pivotally engaging therethrough upon engagement of ears 126, 128, around cap body 134 and engagement of bracket plates 140, 142 against the upper portion of column tubular element 50A. Hence, splint member 44 is pivotable relative to upright column 50 about pivot bolt axle 150.

As shown in FIGS. 11A and 11B, further pivot means 152 is provided to follow splint arm 44 at a selected angular value relative to column member 50, e.g. at discrete angular values selected from 30°, 45°, 60° and 75°. Pivot means 152 includes a screw member 154 and a nut member 156, having opposite end yoke connectors 158, 160, respectively. Screw member yoke connector 158 defines two transversely spaced ears 162, 162, each having a transverse bore 166, 166. Both ears 162 are sized to transversely fit into the hollow 120A of cross-sectionally U-shape splint member yoke section body 120. Bores 124 and 166 are sized and shaped to accommodate a bolt 168 to pivotally releasably interconnect screw member 154 to splint member body 120 about the thus formed pivot bolt axle 168 engaging bore 124.

Screw member 154 further defines a male threaded shaft 170 opposite ears 166, and nut member 156 defines female threaded socket 172 sized and shaped to threadingly accommodate threaded shaft 170.

It is understood that upon threading interengagement of shaft 170 into socket 172, the overall length of the combination of screw member 154 and nut member 156 will vary, i.e. can be adjusted by rotation of one of screw member 154 or nut member 156 relative to the other.

An L-shaped anchor plate 174 is further provided defining an intermediate bore 176 and two opposite bores 178 and 180. Nut member yoke connectors 160 each includes a transverse bore 164, 164, transversely pivotally engaged by a bolt 182. Anchor plate 174 is engaged between ears 160 in such a fashion that anchor plate bore 180 come in transverse register with nut member bores 164 and is transversely engaged by bolt 182, while anchor plate bores 176 and 178 clear nut member yoke section 160.

As best seen in FIGS. 11A and 17A, anchor plate bores 176 and 178 are engaged by corresponding pins 185 and 187 which engage a selected one of lengthwisely spaced cavities 183, 183' (FIG. 17A) made in a top portion of male telescopic tubular member 50C, while one transverse leg 174A of L-shape anchor plate 174 projects transversely outwardly from male member 50C through a registering aperture 184 in the wall of female telescopic member 50A. Nuts 179 cooperate with bolts 168, 180 and 182 to lock them as stated above.

It can now be understood from the sequence of FIGS. 5A, 11B and 17A, that the overall length of threadingly interconnected screw member 154 and nut member 156 is progressively adjustably reduced by rotation of one of members 154 or 156 relative to the other. The L-shape anchor plate 174 will carry telescopic member 50C in a downward sliding motion away from pivotal bolt axle 150 and from the hollow of tubular female member 50A, pivotally bringing therein the inner portion of splint arm 44 adjacent pivot axle 150, so that the angular value between splint member 44 and column member 50 decreases from a large angular value $\Theta 1$ (FIG. 5A) to a slightly smaller angular value of $\Theta 2$ (FIG. 11B), down to a still smaller angular value $\Theta 3$ (FIG. 17A).

In one embodiment, telescopic male tubular member 50C will have a series of lengthwisely spaced transverse bores 190, 190', 190", 190''', ... adapted to come in register with a bore 192 made transversely through an intermediate section of female tubular member 50A, wherein bores 192 and a selected one of bores 190, 190', ... will become releasably engaged by a pin 194 sized and shaped for engagement therethrough. As the angular value of splint member 44 relative to column member 50 shifts from $\Theta 1$ to $\Theta 2$ to $\Theta 3$, pin 194 is released from bottom bore 190''' and moved to intermediate bore 190' and eventually to top bore 190 of column member male telescopic tubular member 50C. In other words, as shown in FIG. 11B, by moving pin 194 into a selected one of bores 192 of tube member 50C, there is modified the patient's injured arm adduction limit angular value, wherein in one embodiment this angular value is selected from discrete values between 30°, 45°, 60° and 75°.

Figure 5C:
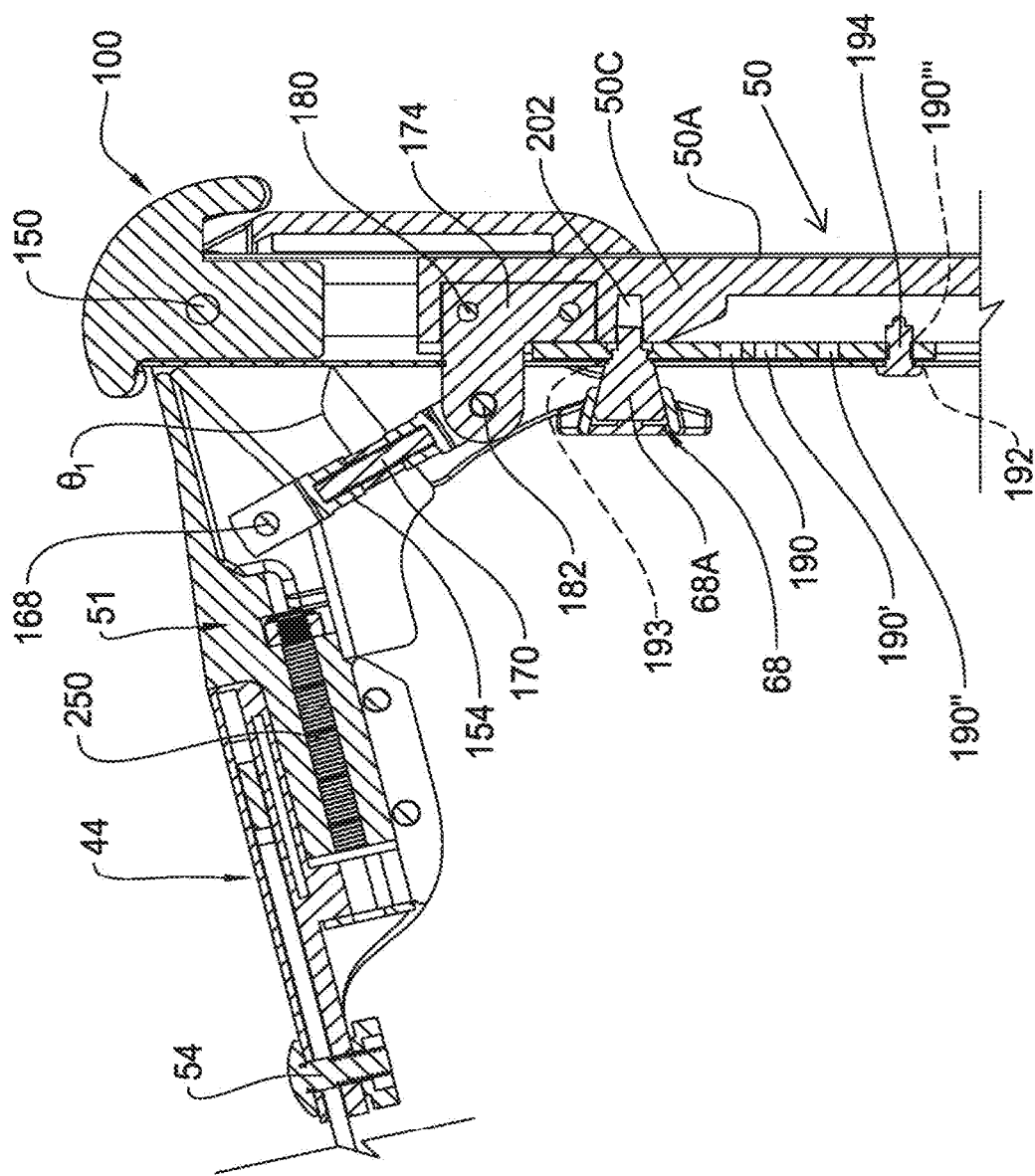
FIG. 5C is a view similar to FIG. 5A but with the spring-loaded twist activated plunger fully engaged transversely into the column member.
Figure 5D:
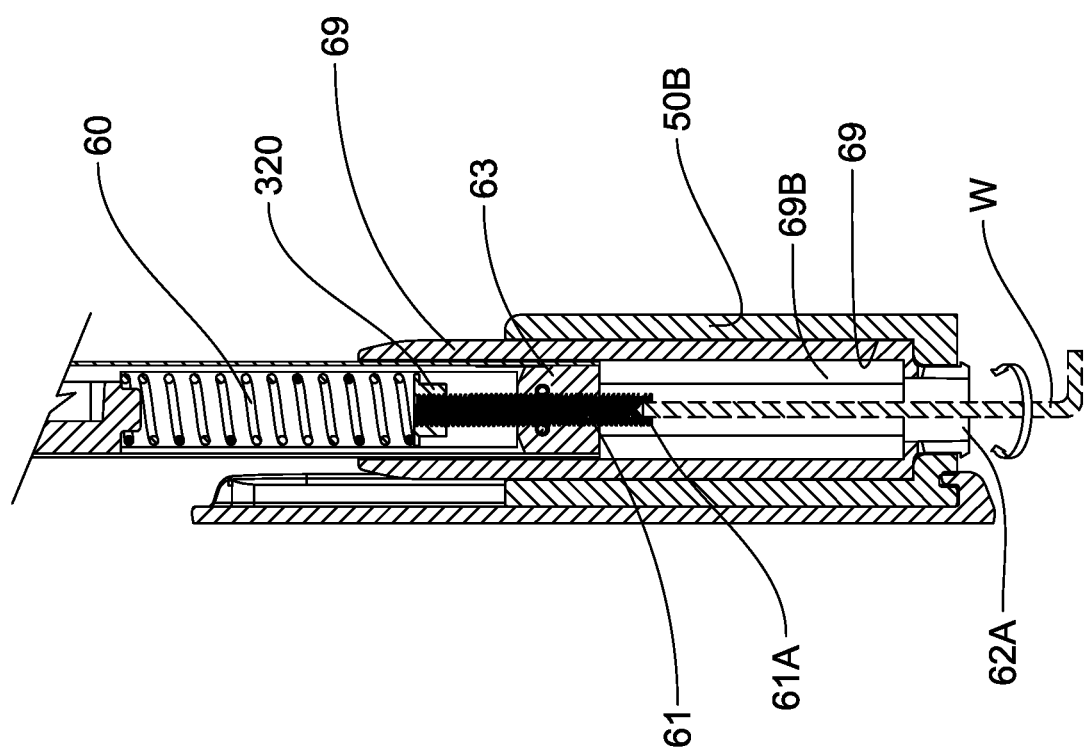
FIG. 5D is an enlarged view of the lower end portion of upright column member, suggesting how a separate Allen key tool may be used to axially rotate the inner axial spring tension adjustment chord.

As best shown in FIGS. 5A and 5C, spring-loaded twist activated plunger 68 defines a main body 68A projecting freely outwardly transversely from tubular member 50A through upper bore 193 of column tubular member 50A and into a frusto-conical cavity 202 made transversely of inner tubular member 50C adjacent anchor plate 174.

FIG. 5A shows spring-loaded twist activated plunger 68 in retracted condition substantially clearing cavity 202, while FIG. 5C shows spring-loaded twist activated plunger 68 in its fully extended condition inside cavity 202. When spring-loaded twist activated plunger 68 is in its fully extended condition inside cavity 202, movement is locked in the position determined by immobilization of pin 194 inside the selected bore 192, forming a patient's injured arm abduction lower limit condition at splint arm 44. The purpose of spring-loaded twist activated plunger 68 is to apply tension on coil spring 60 in the conditioning exercising mode of the present orthosis. Upon release of spring-loaded twist activated plunger 68 (FIG. 5A), coil spring 60 is also released or freed. Pin 194 will set a lower threshold limit stop determining minimal angular inclination between pivotal arm 44 relative to upright column 50, the purpose of this being to minimize risk of muscular fibers damage for the patient's injured muscle or tendon. Arm 44 may be lowered against spring bias from column spring 60, which enables muscular reinforcement conditioning exercise, wherein muscular rehabilitation is promoted. Patient's uninjured muscles thereby benefit from conditioning exercise.

Spring-loaded twist activated plunger 68 will be released from top tubular element 50A to enable conditioning exercise at any angular value such as Θ1, Θ2 and Θ3 as adjusted by pin 194 and as prescribed by the medical specialist.

Thus, according to an embodiment of the present invention, the gas cylinder of the re-adaptation mechanism of U.S. Pat. No. 9,204,989 is replaced by a pre-stressed mechanical coil spring 60 whose stress level is adjustable. Such an adjustable mechanism of rehabilitation allows the orthosis to dynamically accompany the progression of the patient's healing over time, allowing to modify (i.e. adjust) progressively and continuously the level of spring stress applied to the patient's muscles. This modified adjustable mechanism also makes it possible to better adapt to the morphology of the patient including size, age, muscle tone, general posture, etc.

In one embodiment in particular, the present orthosis is adapted to fit patients height ranging e.g. from 5 to 6.5 feet (i.e. about 1.5 meter to 2 meters).

The present invention thus relates to an abduction orthosis 40, properly anchored around a patient's waist. With the present dynamic arm support orthosis, the patient's arm is strapped to a forearm trough or cradle member 46, which is mechanically coupled to a waistband belt 43 anchored around the waist of the patient. The coupling between the forearm trough 46 and waistband belt 43 can be adjusted. The patient's arm and hand are held in a cosmetically pleasing pose, and the patient's hand from the injured patient's arm is available for use, enabling early functional recovery. The dynamic arm and shoulder support orthosis is easy to put on and take off, and full de-weighting of the patient's arm is feasible.

Rehabilitation exercises are thus performed in the patient's frontal plane. There is integration of the rehabilitation mechanism (column member axial spring 60) in the hip-shoulder column member 50. There is also adjustment of the resistance of the rehabilitation mechanism by a screw means 61-63 integrated in the hip joint.

The waist band 43 in the present shoulder orthosis 40 prevents anterior migration that is common with prior art shoulder braces for injured football players or gymnasts.

Contra-lateral suspension from the uninjured shoulder S' supported sling band 80 is comfortable and secure, resists displacement while allowing a broad range of independent patient's activities. In one embodiment, a wide-sculpted sling band 80 is provided, to enhance comfort for promoting treatment compliance.

The forearm and hand rest in carefully contoured cradle members 46, 81, respectively. A pair of padded loop straps 360 (FIG. 21) around patient's injured arm and attached to cradle member 46 may be added so that patient's arm and splint 40 become integral during treatment, so as to avoid accidental release.

The device is worn by the patient inconspicuously under a garment, is useful either during mobility, while seated or when recumbent, and is applicable to human beings whose willful control of the shoulder joint is absent or decreased as the result of illness or injury.

The invention claimed is:

1. Shoulder orthosis for support of a patient's arm in a postoperative angularly adjustable shoulder immobilization abduction posture in a context of injured rotator cuff muscle tear, said orthosis comprising:
   a waistband belt member, for adjustably fitting around the patient's waist, and defining a belt support section;
   a splint, defining a rigid main body having opposite outer and inner end portions, for removably supporting a patient's injured arm;
   an elongated column member, defining top and bottom end portions, said bottom end portion thereof anchored to said belt support section and said top end portion thereof anchored to said inner end portion of the splint;
   joint means interconnecting said splint inner end portion to said column member top end portion for relative movement of said splint thereabout;
   telescopic extension means providing adjustable extension of the length of said elongated column member;
   biasing means, cooperating with said column member in providing resistance to patient's injured arm adduction at said splint, said biasing means consists of an axial spring means cooperating with said column member and biasing said splint away from said waistband belt member, said spring means allows cyclical extension/retraction of the adjustable length column member between opposite first and second limit conditions thereof; characterized in that said column member configured to remain closely spacedly applied against the patient's torso during movements of the splint relative to the patient's waistband belt, said axial spring means continuously biases said splint to an abduction lower limit position, in accordance with the type of medical condition surgery, for stable support of the patient's injured forearm around a horizontal plane, while allowing pivotal movement of the patient's injured arm about a generally vertical axis intersecting the patient's elbow and approaching that patient's torso;
   locking means, applying tension on said biasing means in a conditioning exercise mode of said orthosis, and releasably locking said column member in a selected angular orientation relative to said splint, whereby said splint forms a cantilever with said column member, said locking means consists of a spring-loaded twist activated plunger, anchoring said axial spring means in an operative condition whereby tension is applied onto said axial spring means in the conditioning exercise mode of said orthosis, and releasing said axial spring means in an inoperative condition thereof, and pin means cooperating with said column member in setting a lower threshold limit stop for minimal angular inclination between said splint relative to said column member; and chord adjustment tensioning means, cooperating with said biasing means in enabling transmission of the patient's injured arm adduction movement at said splint;

wherein said orthosis allows the cyclical exercise of the healthy adductor muscles of the patient's injured arm while minimizing the contraction of the injured arm rotator cuff muscles.

2. A shoulder orthosis as in claim 1, wherein said axial spring means consists of an elongated compression coil spring member coaxially mounted lengthwisely inside said column member within a telescopic female tubular member therein, and engaging at its top end a male tubular member within said female tubular member and said chord adjustment tensioning means being an internal chord at a bottom end thereof carried by a seat transversely mounted integral to said column member bottom end portion, characterized in that said internal chord provides transmission of the adduction movement, while said coil spring member inside said column member provides resistance to adduction of the patient's injured arm.

3. A shoulder orthosis as in claim 2, wherein said joint means provides internal and external rotation capability of the splint main body relative to said column member.

4. A shoulder orthosis as in claim 3, wherein said joint means further provides angular tilt capability of the splint main body relative to said column member, whereby said splint main body is movable in translation between a first fully extended abduction limit condition and a second retracted adduction limit condition, angularly with respect to the patient's torso.

5. A shoulder orthosis as in claim 2, wherein said joint means provides angular tilt capability of the splint main body relative to said column member.

6. A shoulder orthosis as in claim 5, wherein said joint means angular tilt capability is selected from the following discrete values: 30°, 45°, 60° and 75°.

7. A shoulder orthosis as in claim 1, wherein said belt member includes a hook and loop fastener means enabling width adjustment of said waistband belt, the latter being also padded for added patient's comfort and adapted for right or left shoulder injuries.

8. A method of using a shoulder orthosis as disclosed in claim 1, wherein said method comprises the following steps:
attaching said waistband belt to the patient's waist;
attaching the patient's arm to said splint;
deactivating said locking means; and
engaging the patient's adductor muscles to at least partially retract said column member from a first fully extended limit condition to a second limit condition thereof;
characterized in that said column member remains closely spacedly applied against the patient's torso during movements of the splint relative to the patient's waistband belt.

9. A shoulder orthosis for support of a patient's arm in a postoperative angularly adjustable shoulder immobilization abduction posture in a context of injured rotator cuff muscle tear, said orthosis comprising:

a waistband belt member, for adjustably fitting around the patient's waist, and defining a belt support section;

a splint, defining a rigid main body having opposite outer and inner end portions, for removably supporting a patient's injured arm;

an elongated column member, defining top and bottom end portions, said bottom end portion thereof anchored to said belt support section and said top end portion thereof anchored to said inner end portion of the splint;

joint means interconnecting said splint inner end portion to said column member top end portion for relative movement of said splint thereabout;

biasing means, cooperating with said column member in providing resistance to the patient's injured arm adduction at said splint;

locking means, applying tension on said biasing means in a conditioning exercise mode of said orthosis, and releasably locking said column member in a selected angular orientation relative to said splint, whereby said splint forms a cantilever with said column member; and chord adjustment tensioning means, cooperating with said biasing means in enabling transmission of the patient's injured arm adduction movement at said splint;

a flexible elongated sling band anchored at one end to a section of said waistband belt and configured to form a loop around the patient's uninjured shoulder at another end thereof opposite said one end thereof: an elongated forearm support cradle, integrally carried at said outer end portion of the splint main body and defining a free end portion opposite said splint main body; wherein said orthosis allows the cyclical exercise of the healthy adductor muscles of the patient's injured arm while minimizing the contraction of the injured arm rotator cuff muscles.

10. A shoulder orthosis as in claim 9, further including a hand-rest member carried by said cradle at said free end portion thereof.

11. A shoulder orthosis as in claim 9, further including multiple moisture ventilation perforations made in said cradle.

12. A shoulder orthosis as in claim 9, further including cradle telescoping means providing adjustable coaxial displacement of said cradle relative to said splint main body.

13. A shoulder orthosis as in claim 12, further including cradle telescopic adjustment means for lengthwise cradle extension/retraction.

14. A shoulder orthosis as in claim 13, further including cradle roll adjustment means cooperating with said cradle telescopic adjustment means for rolling motion of said cradle.

* * * * *